United States Patent
Hansen et al.

(10) Patent No.: US 12,221,643 B2
(45) Date of Patent: *Feb. 11, 2025

(54) CONVERSION OF LIGNOCELLULOSIC BIOMASS INTO BIOGAS

(71) Applicants: Jaron C. Hansen, Springville, UT (US); Lee D Hansen, Saratoga Springs, UT (US); Zachary T Aanderud, Provo, UT (US); Conly L Hansen, N. Logan, UT (US)

(72) Inventors: Jaron C. Hansen, Springville, UT (US); Lee D Hansen, Saratoga Springs, UT (US); Zachary T Aanderud, Provo, UT (US); Conly L Hansen, N. Logan, UT (US)

(*) Notice: Subject to any disclaimer, the term of this patent is extended or adjusted under 35 U.S.C. 154(b) by 207 days.

This patent is subject to a terminal disclaimer.

(21) Appl. No.: 17/706,569

(22) Filed: Mar. 28, 2022

(65) Prior Publication Data
US 2022/0220517 A1    Jul. 14, 2022

Related U.S. Application Data

(60) Division of application No. 16/875,977, filed on May 15, 2020, now Pat. No. 11,365,433, which is a
(Continued)

(51) Int. Cl.
*C12P 7/54* (2006.01)
*C12M 1/00* (2006.01)
(Continued)

(52) U.S. Cl.
CPC ............ *C12P 7/54* (2013.01); *C12M 27/06* (2013.01); *C12M 29/24* (2013.01); *C12P 5/023* (2013.01);
(Continued)

(58) Field of Classification Search
None
See application file for complete search history.

(56) References Cited

U.S. PATENT DOCUMENTS 3,711,392 A * 1/1973 Metzger .................... C12P 7/06
                                                                  210/603
4,318,993 A * 3/1982 Ghosh .................... C12M 21/04
                                                                  210/603
(Continued)

OTHER PUBLICATIONS

Mamimin et al. "Two-stage thermophilic fermentation and mesophilic methanogen process for biohythane production from palm oil mill effluent." International Journal of Hydrogen Energy, 40 (2015), pp. 6319-6328. (Year: 2014).*
(Continued)

*Primary Examiner* — William H. Beisner
(74) *Attorney, Agent, or Firm* — L. Alan Collins

(57) ABSTRACT

A method for biogas production includes feeding a receiving structure with a feed containing biomass that comprises lignocellulose and directing the feed from the receiving structure into an anaerobic secretome bioreactor (ASB) reactor environment which includes a synthetic microbial community consisting of at least one selected from extremophile thermophilic anaerobic microorganisms that are essentially acidogens and acetogens, the synthetic microbial community producing a secretome of exozymes. The ASB treated biomass is further directed to an aerobic digestion (AD) reactor environment, the ASB treated biomass being pasteurized so as to be essentially free of non-thermophilic microorganisms, the ASB treated biomass comprising liquid effluent containing solubilized biomass products and metabolized biomass products, and solid effluent. Contents or heat are recycled through a conduit between the ASB reactor environment and the AD reactor environment.

20 Claims, 12 Drawing Sheets

Related U.S. Application Data continuation-in-part of application No. 16/194,271, filed on Nov. 16, 2018, now abandoned, application No. 17/706,569, filed on Mar. 28, 2022 is a division of application No. PCT/US2018/061695, filed on Nov. 16, 2018.

(60) Provisional application No. 62/750,221, filed on Oct. 24, 2018, provisional application No. 62/587,417, filed on Nov. 16, 2017.

(51) Int. Cl.
*C12M 1/06* (2006.01)
*C12P 5/02* (2006.01)
*C12P 7/42* (2006.01)
*C12P 7/56* (2006.01)

(52) U.S. Cl.
CPC .................... *C12P 7/42* (2013.01); *C12P 7/56* (2013.01); *C12P 2203/00* (2013.01)

(56) References Cited

U.S. PATENT DOCUMENTS

| 11,365,433 | B2* | 6/2022 | Hansen | C12P 5/023 |
| 2009/0107913 | A1* | 4/2009 | Johnson | C12P 3/00 |
| | | | | 210/603 |
| 2010/0093046 | A1* | 4/2010 | Remmereit | C12M 21/02 |
| | | | | 435/162 |
| 2016/0186072 | A1* | 6/2016 | Lehoux | C10G 2/32 |
| | | | | 435/167 |

OTHER PUBLICATIONS

Abreu et al. "Boosting dark fermentation with co-cultures of extreme thermophiles for biohythane production from garden waste", Bioresource Technology 219 (2016) 132-138. (Year: 2016).*

Pakarinen et al. "One-stage H2 and CH4 and two-stage H2DCH4 production from grass silage and from solid and liquid fractions of NaOH pre-treated grass silage", Biomass and Bioenergy 33 (2009) 1419-1427. (Year: 2009).*

Schonberg et al. "The influence of the temperature regime on the formation of methane in a two-phase anaerobic digestion process", Eng Lfe Sci. 2012, 12, No. 3, 279-286. (Year: 2012).*

\* cited by examiner

CONVERSION OF LIGNOCELLULOSIC BIOMASS INTO BIOGAS

CROSS REFERENCE TO RELATED APPLICATIONS

This application is a divisional application of continuation-in-part U.S. patent application Ser. No. 16/875,977 filed on May 15, 2020, which is a continuation-in-part of U.S. patent application Ser. No. 16/194,271, filed Nov. 16, 2018, which claims priority from U.S. Provisional Application 62/750,221 filed Oct. 24, 2018 and U.S. Provisional Application 62/587,417 filed Nov. 16, 2017, all of which are hereby incorporated by reference. This application also claims priority to PCT/US18/61695 which claims priority from United States Provisional Application 62/750,221 filed Oct. 24, 2018 and U.S. Provisional Application 62/587,417 filed Nov. 16, 2017, all of which are hereby incorporated by reference.

BACKGROUND

Anaerobic digestion is used to convert soluble products into biogas which can be used to generate fuels, chemicals, fibers, and energy. To be economically viable, and reduce the amount of unconverted biomass waste, an adequate conversion percentage is desirable. A major problem arises in the digestion of lignocellulosic waste. Lignin is generally considered not available to anaerobic digestion and is largely not converted. The use of multiple anaerobic digesters to convert biomass into biogas has been suggested but none of these digestion systems are designed specifically to digest lignin, and with these systems most lignocellulose remains undigestible.

Lignocellulosic biomass is a relatively inexpensive, renewable, and abundant material. However, without some kind of chemical or mechanical processing of lignocellulosic biomass, anaerobic digestion typically converts only one-third of the carbon in the lignocellulosic biomass into biogas. In addition, the biogas is typically only 60% methane. Anaerobic digestion by microorganisms is effective on hemicellulose-side chains, but in lignocellulosic biomass that contains cellulose, long glucose chains, these chains are only slowly digested. Further, lignin, a complex polyphenol that can be abundant in plant biomass, is resistant or toxic to many microorganisms.

DETAILED DESCRIPTION

Figure 1:
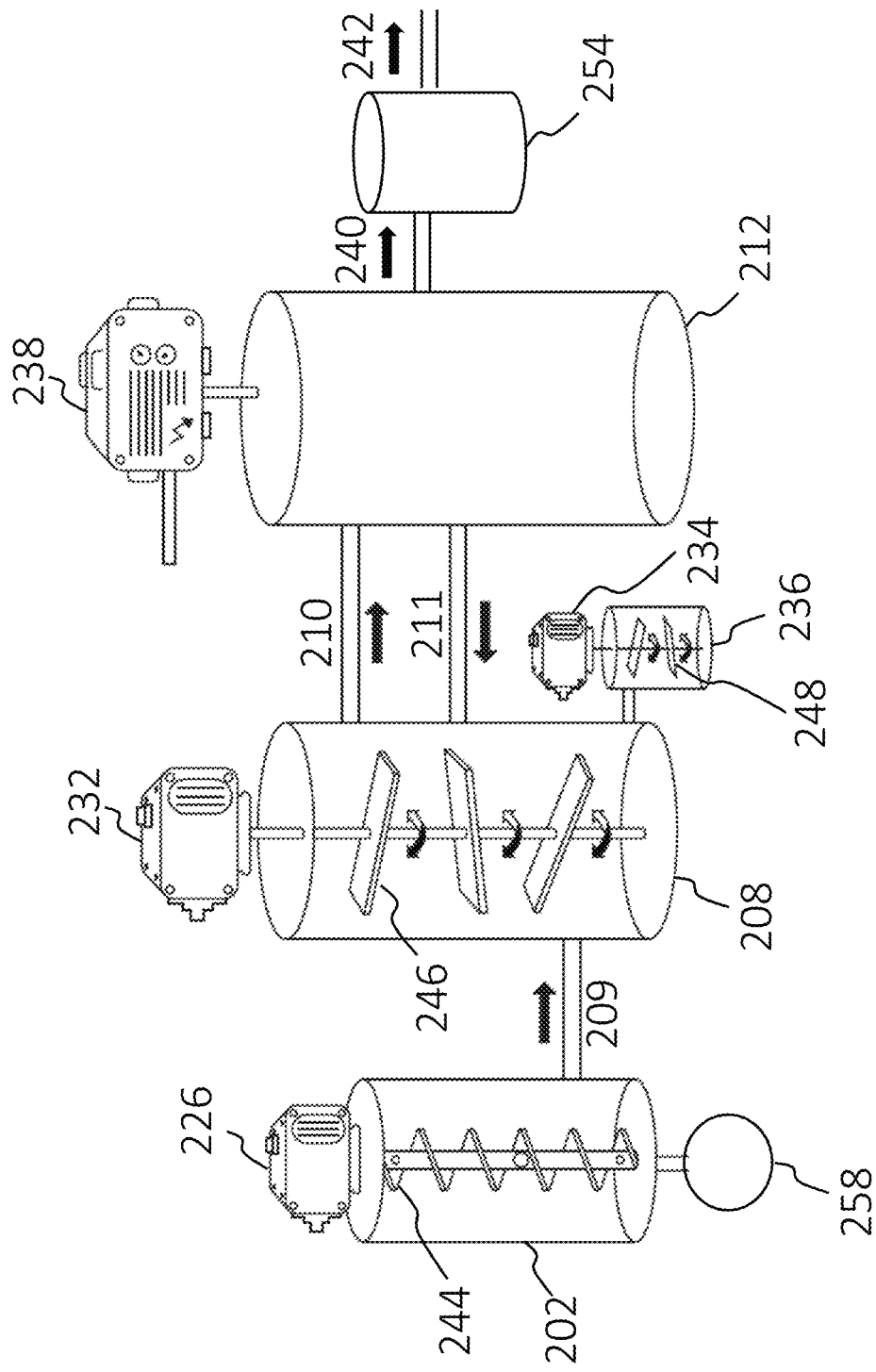
FIG. 1 illustrates a diagram of an example reactor according to principles described herein.

The following describes two successive anaerobic digestion environments that are used to treat lignocellulosic biomass;

(1) a high-temperature biological anaerobic digestion environment by thermophilic anaerobic microorganisms and pasteurization of non-thermophilic anaerobes or mesophilic anaerobes. This digestion is described here as an anaerobic secretome bioreaction (ASB) environment.

(2) an anaerobic digestion (AD) environment with non-thermophilic or mesophilic anaerobes. An example anaerobic digestion system according to principles discussed herein includes an ASB environment and an AD environment. The system treats biomass for the production of biogas and includes structure adapted to receive a feed containing biomass. The ASB environment contains thermophilic anaerobic microorganisms that can only exist at thermophilic ASB temperature conditions, but thrive and digest lignocellulose. The thermophilic anaerobic microbes metabolize and solubilize the biomass through hydrolysis, acidogenesis, and acetogenesis to produce products accessible for digestion. These products include several products, but typically comprise one or more of acetic acid and lactic acid. As more fully described below, the ASB environment can be adjusted to favor acetic acid production over lactic acid production, or vice versa. This in turn determines the amount of $CO_2$ in the biogas product. Accordingly, an essentially $CO_2$ free biogas, or a biogas with a predetermined $CO_2$ content can be produced.

The ASB environment is of a thermophilic temperature to support growth of the thermophilic anaerobic organisms. The thermophilic anaerobic microorganisms thrive at temperatures sufficiently high to damage or kill non-thermophilic or mesophilic microorganisms. The ASB temperatures accordingly pasteurize the biomass of non-thermophilic microbes.

A benefit of the ASB temperature, in addition to providing optimization for thermophiles and the advantage of pasteurization, is that the growth and pasteurization occurs at a faster rate than would be achieved at a non-thermophilic temperature.

Because of the pasteurization, the ASB environment is essentially free of non-thermophilic or mesophilic (NT) microbes. NT microbes include those commonly used in conventional or prior-art treatments and may occur naturally in biomass materials. NT microbes may also include common pathogens in lignocellulosic waste streams, such as manure. NT microbes do not thrive, or usually even survive, thermophilic temperatures. Specific examples of NT microbes include *E. coli, Salmonella typhimurium, Salmonella* Dublin, *Campylobacter* spp., *Listeria monocytogenes, Yersinia enterocolitica, Cryptosporidium parvum, Giardia lamblia, Enterococcus*, fecal coliform, and enterobacteria. Other examples are anticipated.

Many prior-art processes produce waste streams that are contaminated with pathogens that were present in the original biomass feed prior to treatment. This creates a disposal problem, as the waste stream may be a pathogenic biohazard that cannot be used for other purposes, such as soil remediation for food-crops. The pasteurization temperatures of the ASB eliminate this problem Structure is provided to remove from the ASB environment, ASB treated biomass comprising solubilized biomass, liquid effluent, and solid effluent from the ASB environment, and introduce it to the anaerobic digestion (AD) environment. This structure may also include structure, such as coolers or heat exchangers, to cool the ASB effluent to a temperature suitable for the AD environment. The heat removed from the ASB effluent may be recycled, as described below, for example to heat future biomass feed for the ASB.

The AD environment is of a temperature to sustain and support growth of NT anaerobic microbes. After the NT anaerobic microbes are pasteurized in the ASB environment and thus become inactive in the AD feed, additional anaerobic microbes must be initially introduced or inoculated into the AD environment for the AD treatment. This may be accomplished by any suitable means, such as a direct, inoculation, or through a satellite reservoir described below. The AD environment is not thermophilic and does not sustain or support growth of thermophilic ASB microorganisms. The NT anaerobic microbes introduced to the AD environment digest the ASB treated biomass through methanogenesis to produce methane. Unlike prior-art anaerobic digestion processes, difficult or impossible to digest lignocellulosic materials in the biomass have been converted in the ASB to readily anaerobic digestible materials for the AD feed. In addition to methanogenesis in the AD, hydrolysis, acidogenesis, acetogenesis, and other processes may also occur.

Moreover, various contents may be introduced or recycled to the ASB environment by the AD environment. Furthermore, at least one satellite reservoir may supply contents to at least one of the ASB and AD environments according to principles described herein.

A heat recovery system may be used to recover and recycle heat from at least one environment. For example, at least one heat exchanger may be used to direct heat from at least one environment to at least one other environment. Purification treatments may also be used on contents produced by at least one environment. Also, contents may be recycled from at least one environment to at least one other environment.

The treatment processes according to principles described herein advantageously have lower energy costs compared to current treatment processes, render biomass significantly more available to anaerobic treatment, and introduce no chemical agents that are poisonous or inhibitory to anaerobic microorganisms. The two-part anaerobic digestion environments described herein are to treat biomass more completely and quickly without the use of mechanical and chemical pretreatment. It is acknowledged that processes are available that use anaerobic digestion by anaerobic microbes to solubilize biomass into materials that can be converted into biogas. The microbes may be readily available and often occur naturally with the biomass. A problem with these processes is that biomass materials often contain significant amounts of lignocellulosic materials that are essentially insoluble under anaerobic digestion.

An example of such a process is disclosed in U.S. Pat. No. 6,342,378 to Zhang, wherein digestion is modified to control volatile fatty acids which can inhibit the conversion to biogas. However, even with this improved digestion system, problems with materials that are unable to be solubilized or digested are significant, as noted in column 8, line 67 through column 9, line 13. Materials like rice straw are difficult to biodegrade. This is due, at least in part, to the plant fibers having lignin, cellulose, and hemi-cellulose, all of which are water-insoluble. Breakdown of these insoluble materials can be achieved to some degree by chemical hydrolysis or biodegradation. However, the breakdown is severely inhibited by lignin, cellulose, and hemi-cellulose which form barriers or seals around materials and which are considered non-biodegradable by conventional digestion.

Efforts have been made to improve anaerobic digestion of biomass by treating biomass with chemical or mechanical means beforehand, however, there are several drawbacks. Mechanical treatment systems, such as grinding and cutting, are generally energy intensive, uneconomical, and only modestly effective in improving conversion. Chemical treatment introduces components, such as acids or bases, to chemically react with biomass and make it more available to anaerobic digestion. These components, however, are often poisonous to anaerobic bacteria and are also only modestly effective. Strong acids or alkalies used to breakdown or damage lignin actually poison the anaerobic digestion. Any advantages from breaking down the biomass components by the chemicals are compromised by causing a less than optimal anaerobic environment in the subsequent anaerobic digestion tank. Chemical means can further create an expensive disposal problem for toxic wastes that result.

There are known microbes that in nature digest lignin, but none have been used in a biomass to biogas system, particularly a system that can be operated on an industrial scale. Because of the ASB treatment prior to the AD treatment, the AD treatment functions in a more efficient and controlled manner that is not achievable in conventional anaerobic treatments. In addition, the ASB treated biomass to the AD is pasteurized, free from problems associated with conventional anaerobic digesters where the composition of the methanogenic consortium cannot be controlled from contamination from unpasteurized feedstock. The ASB treatment thus allows customization and optimization of the AD anaerobic microorganisms, depending on, for example, the nature of the biomass, process conditions, and other variables.

In contrast to conventional anaerobic digestion, any of certain suitable thermophilic microorganisms that digest lignocellulosic materials can be used in the ASB to biologically treat biomass fed to the AD to make it significantly more available to anaerobic digestion. The ASB may occur in a suitable reactor or tank, or any other environment that produces an effluent comprising at least one of a solubilized biomass, liquid effluent, and solid effluent.

The ASB environment provides an environment where microbes can thrive without compromising the environment for subsequent treatment in the AD environment by anaerobic methanogenetic microbes. Example microorganisms suitable for the ASB include bacteria or organisms capable of breaking down lignocellulose (e.g., cellulose, hemicellulose, lignin, etc.). Examples include thermophilic extremophiles found naturally in some hydrothermal pools. A study indicated that the bacteria anaerobic thermophile *Caldicellulosiruptor bescii* ("*C. bescii*") solubilizes 85% of lignocellulose and cellular material. (See "Carbohydrate and lignin are simultaneously solubilized from untreated switchgrass by microbial action at high temperature," Energy and Environmental Science, Issue 7, 2013.)

The principles described herein may be applied to carry out the reaction on an industrial scale, providing universal industrial conversion of biomass by extremely thermophilic microbes in a treatment that requires limited or no chemical additions. The ASB/AD digestion is suitable for any biomass containing lignocellulosic materials. Other hard to digest materials, such as bacterial cell material and algae may also be advantageously digested by the ASB/AS system. In an example, the ASB/AD digestion is applied to giant king grass, mixed green waste, paper, sewage, manure and/or several other feedstocks on a pilot plant scale. In another example, the ASB/AD digestion is scaled to commercial anaerobic digestion systems, such as electrical generation on a megawatt scale.

The environment suitable for organisms, such as *C. bescii*, to thrive and produce sufficiently large amounts of secretome, is thermophillic. For example, in a lab experiment, *C. bescii* solubilized up to 90% of lignocellulose and cellular material in an ASB environment to make the carbon accessible for anaerobic digestion. Accordingly, the biomass is heated, either in a previous tank, or in the ASB tank, to a high temperature that is suitable for the growth and flourishing of ASB organisms. The ASB environment is unsuitable for growth of anaerobic organisms usually found in conventional anaerobic digestion. Accordingly, the biomass is effectively pasteurized, with the exception of the ASB organisms.

The AD is operated in a similar manner as a conventional anaerobic digestion system. But, there are significant differences that derive from its use together with the ASB. Among others, the AD receives a non-conventional lignocellosic-depleted and optimized predigested feed that can there be more fully digested and converted to biogas.

Anaerobic digestion involves at least four processes—hydrolysis, acidogenesis, acetogenesis, and methanogenesis (biogas generation). A single anaerobic digestion cannot be optimized for all such processes. By separating digestion into two environments, processes such as hydrolysis, acidogenesis, acetogenesis in the ASB can be more quickly and more completely carried out, thus creating an ideal and readily available biomass for methanogenetic biogas generation in the AD.

The combined ASB and AD is an improved digestion reactor system which can achieve a much higher biogas conversion than a conventional anaerobic system. By digesting the biogas in two radically different anaerobic environments, rather than one, a more complete digestion of the biomass is achieved.

Summary of ASB/AD Digestion System and Method

The ASB/AD digestion systems and methods have several advantages and differences over known anaerobic digestion systems, which will be described below and which include, but are not limited to:

Separation into two anaerobic digestion environments, a hot thermophilic ASB and a cooler AD,
Modification of AD feed by ASB converting lignocellulosic materials to digestible materials,
Material increase of the portion of biomass converted to biogas, and the rate of conversion. (see Examples below "TESTS OF DIGESTION SYSTEM")
Control in ASB environment of anaerobic microbes by pasteurization of all but thermophilic anaerobes and elimination of pathogenic organisms.
The ability to approach or achieve a closed system with a minimum number of added reagents by, for example, recycling of carbonate, low energy consumption by heating from biogas combustion, etc. Several other material and energy recycle options are available.
The ability to select between $CO_2$ free biogas and $CO_2$ containing biogas production.

Definitions

The term "thermophilic" with respect to the ASB environment describes an environment where thermophiles or thermophilic microbes thrive, and NT microbes are killed or damaged. This can be a temperature above about 45 to 65° C., and includes temperatures at which extreme thermophiles thrive, such as 70° C.-75° C. and above. NT microbes, which include mesophilic microbes generally used in prior art biomass digestion processes at temperatures between 20 to 45° C. are killed or damaged in a thermophilic environment. Moreover, the thermophilic temperature is fatal to any microbes that are not adapted to high temperatures commonly found in natural thermal springs or pools which can have temperatures of, for example 70° C., 70-75° C., or 75° C. and greater.

The term "tank" refers to an actual tank or other reaction containment, space or environment in which suitable conditions are met. The term further includes a suitable continuous or semi-continuous flow reactor, plug-flow reactor, reaction tank, etc.

The term "reactor" refers to at least one tank or set of tanks used in relation to the treatment of lignocellulosic biomass.

The term "satellite reservoir" refers to a separate, independent reservoir that is configured to maintain and provide at least one microbe, nutrient solution, pH adjusting chemical, or other content to another environment.

The term "environment" is broadly used to include environments that include not only tanks and reservoirs, but other environments for applying principles discussed herein. Note that "tank", "reactor", "environment," and "satellite reservoir" may be used interchangeably according to principles discussed herein. Each may further perform at least one of mixing and heating according to principles described herein. ASB and AD may be described in association with an environment or more generally as a process.

The term "biogas" refers to gas which may be combusted to generate electricity and heat, or further processed into renewable natural gas and transportation fuels. Biogas as described herein may include at least one of methane, pure methane, carbon dioxide, compressed natural gas (CNG), and other contents known or as described herein.

EXAMPLES

Tests of ASB/AD Digestion System

Example—Dairy Manure Testing Results

A 6% solids solution of dairy manure was ASB treated in the ASB tank for 48 hours. After ASB treatment, the material was anaerobically digested and the rate of biogas production and composition was measured. A control experiment was conducted by heating a 6% solids solution of dairy manure to 75° C. for 48 hours. Afterward, the solution was anaerobically digested and the rate of biogas production and composition was measured. FIG. 12A shows that ASB treated manure (solid black line) produced 2.5× more biogas than the control (dashed black line). FIG. 12B shows the rate of biogas production. The maximum rate of biogas production from ASB treated manure (filled black circles) was 2.7× larger than the maximum rate of biogas production from the control (filled black triangles). The methane content in ASB treated, anaerobically digested manure was 74% compared to 72% for the control.

Example—Waste Activated Sludge (WAS) Testing Results

A 5% solids solution of WAS was ASB treated in the ASB for 48 hours. After ASB treatment, the material was anaerobically digested and the rate of biogas production and composition was measured. A control experiment was conducted by heating a 6% solids solution of WAS to 75° C. for 48 hours. Afterward, the solution was anaerobically digested and the rate of biogas production and composition was measured. FIG. A reproduced below shows ASB treated WAS (solid black line) produced 2.4× more biogas than the control (dashed black line). FIG. B reproduced below shows the rate of biogas production. The maximum rate of biogas production from ASB treated WAS (filled black circles) was 2.6× larger than the maximum rate of biogas production from the control (filled black triangles). The methane content in ASB treated, anaerobically digested WAS was 76% compared to 62% for the control. Clearly, it can be appreciated that the treated biomass increases biogas production.

ASB/AD Bioreactor System

ASB Tank

In an example, an ASB tank receives biomass to carry out digestion. Turning to FIG. 1, an example reactor is shown in which biomass 258 is first supplied to a mixing tank 202. The biomass 258 within the mixing tank 202 is mixed with a mixer as represented by paddles 244 and powered by a mixing motor 226. The biomass effluent 209 produced by the mixing tank 202 is supplied to the ASB tank 208 as indicated by a black arrow. Note that at least one of water, heat, and mixing may be applied to the biomass 258 prior to entering the mixing tank 202. In another example, the biomass 258 is fed directly to the ASB tank 208 without the mixing tank 202.

The contents within the example ASB tank 208 are digested and may further be mixed with a mixer as represented by paddles 246 and powered by a mixing motor 232. Heat may also be applied in the ASB tank 208. ASB treated biomass 210 that is produced by the ASB tank 208 is supplied to the AD tank 212 for anaerobic digestion as indicated by a black arrow. The ASB tank 208 may further receive a supply of contents from the ASB satellite reservoir 236 that is functionally connected to the ASB tank 208 and powered by an ASB satellite motor 234. Satellite paddles 248 as shown may be used to stir its contents, such as at least one or more of bacteria, nutrients, and other matter described herein to facilitate the ASB treatment process within the ASB tank 208. Heat may also be applied to the ASB satellite reservoir 236.

In an example, contents such as $CO_2$ and bicarbonate 211 that are produced in the AD tank 212 as powered by motor 238 are recycled back to the ASB tank 208 as indicated by a black arrow. Mixing may also occur in the AD tank 212, as provided by paddles 246. The AD treated biomass 240 is supplied to a biogas processor 254 which produces biogas 242.

The biomass effluent 209 provided to the ASB tank 208 may contain or be at levels approximating, for example, 10% of the influent solids content. Digestion within the ASB tank 208 is accomplished by a secretome of a class of high-temperature thermophilic microorganisms that cannot be present in sufficient numbers in conventional anaerobic digestion. A secretome is the set of proteins expressed by an organism and secreted into the extracellular space or onto the surface of the organism. Any secretome and digestion proteins produced by anaerobic microorganisms used in conventional anaerobic digestion only modestly react and break down biomass, thus achieving only the modest result that has been seen with current anaerobic digestion processes.

Within the ASB tank 208, the biomass effluent 209 receives exposure to at least one material comprising a thermophilic anaerobic microbe that digests and "solubilizes" at least a portion of the biomass effluent 209, including lignocellulose materials, essentially breaking down plant cell structure/walls within the material and making contents of the plant cells available for subsequent anaerobic digestion.

"Lignocellulose" or "lignocellulosic" is meant to describe materials that contain lignin, hemi-cellulose, and/or cellulose that are predominately not solubilized by NT microbes. These materials are not solubilized or are only partially solubilized, leaving a major portion as non-solubilized material that is not available to conversion to biogas. As discussed above, attempts to make these materials available to NT microbes often involve, for example, chemical and mechanical treatment, which is not necessary in the ASB tank 208 according to principles described herein.

Contents introduced into the ASB tank 208 having lignocellulosic biomass may include at least one of animal waste, human waste (e.g., biosolids, etc.), fats, oils, and grease (FOG); food waste/garbage, organic matter, plant matter (e.g., green waste, bio-energy crops, coconut husk, grass, etc.), waste activated sludge (WAS), and algae (e.g. algae grown in reactors, etc.), as well as other contents that may be digested and solubilized. Note that lignocellulosic biomass and other types of raw material or feedstock may be introduced into the ASB tank 208 being pre-mixed together (e.g., in the mixing tank 202, previously mixed before entering the mixing tank 202, mixed before entering the ASB tank 208, etc.) or added separately.

Besides lignocellulosic biomass, biomass effluent 209 contents may include non-lignocellulose biomass and waste paper that does not have lignin, such as slaughterhouse waste, bacteria cell walls that are sluffed off from a ruminant animal, waste activated sludge (WAS), algae, king's grass, waste paper, etc.

While anaerobic digestion by itself is effective, for example, on hemicellulose side chains, other chains like long cellulose chains are only slowly digested by anaerobic bacteria, and polyphenols like lignin are resistant or toxic to many microorganisms. The ASB tank 208 can access the chains and compounds inaccessible to prior art systems to solubilize the long cellulose chains and polyphenols. The use of thermophilic microbes solubilize biomass, up to 90% or more of lignocellulosic materials, making the carbon in the biomass accessible for anaerobic digestion.

The ASB tank 208 includes thermophiles that solubilize lignocellulose and other difficult to digest contents to produce products suitable for anaerobic digestion. The ASB tank 208 further includes at least a basic bicarbonate or other bicarbonate to promote production of biomass products suitable for the AD tank 212 and lower the concentration of lactic and acetic acids in the biomass products. The ASB tank 208 relationship with the AD tank 212 can be likened to a stomach to an intestine, both the ASB tank 208 and a stomach enhancing breakdown of contents for additional processing in the AD tank 212 and intestine. The thermophilic microbes in the ASB tank 208 can readily digest these materials under the thermophilic conditions.

The result is a biomass where a major portion of the lignocellulosic materials are converted (e.g., solubilized, metabolized, etc.) to at least one of lactic acid and acetic acid, which are then readily converted to biogas. In an example, the thermophilic anaerobic microbe is *C. bescii* or another bacteria. Possible other bacteria candidates for the ASB tank 208 include bacteria of at least one of the genus *Caldicellulosiruptor, Clostridium thermocellum*, and *Thermoanaerobacterium saccharolyticum*, and other bacteria with comparable or otherwise suitable properties for digesting at least one lignocellulosic material.

In another example, at least one of fungi, archaea, cellular organism, and an organism or mixture of organisms with comparable or otherwise suitable properties for digesting a lignocellulosic material is used.

At least one of the bacteria or other examples listed as candidates may be in a genetically modified form. In another example, at least one of the bacteria or other examples listed is found in at least one of a hot spring, a concentration of rotting wood, and a lignocellulose-degrading extremophile. The ASB tank 208 may find further use in medical industries. Viruses like those for flu and COVID-19 are inactivated through the ASB treatment. In an example, the virus is subject to two to three days at a temperature of 75° C.

The thermophilic anaerobic bacteria are adapted to derive energy from organic materials that happen to exist in the thermal pools, which are often the unsolubilized remains of wood. It has been found that the lignin/cellulosic materials in biomass can be digested by these same microbes in an industrial scale process that shows dramatically improved conversion of biomass to biogas, both in terms of short treatment times, and the high portion of biomass converted.

Unlike a system in which various compounds are metabolized in an oxygen-free environment, ASB conditions and microbes are chosen to target normally inaccessible ligneous and cellulosic portions of the biomass compounds. The contents in the ASB tank 208 are heated to become environmentally suitable for thermophile, i.e., thermophilic microbial action. Under these conditions, the contents introduced to the ASB tank 208 are pasteurized, eliminating a substantial portion of, or all of, the microbes except for thermophilic bacteria that survive and thrive under ASB heated conditions. This culture of thermophilic bacteria digests lignocellulosic materials, including materials previously inaccessible to other anaerobic digestion and creates an enhanced feed for the anaerobic digestion tank.

For the thermophile to thrive, consideration is taken for a desirable temperature. During the digestion process within the ASB tank 208, the ASB tank 208 is maintained at a desired temperature to provide a suitable environment for the *C. bescii* or other microbes to solubilize cellulose. An example temperature maintained may include 75° C. or approximately 75° C. In another example, a temperature range is maintained, for example, between 45-65° C., or 45-85° C. Narrower ranges include 45-50° C., 50-55° C., 55-60° C., 60-65° C., 65-70° C., 70-75° C., 75-80° C., 80-85° C., 60-70° C., 70-80° C., 70-85° C., or 60-85° C., or other ranges that are used for pasteurization of conventional anaerobic microbes and growth of ASB thermophilic anaerobic microbes. The higher temperature causes the reactions within the ASB tank 208 to go faster than non-thermophilic temperatures and can be done without killing ASB thermophilic anaerobic microbes, enzymes, and other microbes.

The ASB tank 208 is heated to maintain the temperature using any suitable means. Heat may be suitably recycled from other environments described herein as well as other environments and other processes, such as waste heat from engines and other mechanical devices, exhaust, combustion gas heat, solar, etc.

Another condition that is considered for the ASB tank 208 is the oxygen limit. The ASB tank 208 is configured to adhere to oxygen limits for *C. bescii*, based on *C. bescii* being a strict anaerobe, which is $pO_2$=0.5%. The ASB may further be configured for higher oxygen levels. For example, *C. bescii* is capable to withstand oxygen levels as high as $pO_2$=20% for 15-20 minutes. In an example, oxygen levels are thus maintained up to 20% for this duration of time.

Another condition for the ASB tank 208 is a suitable pH that should be maintained for the ASB bacterial growth, such as a range between 4.5 to 8.5. For optimal growth of *C. bescii*, the pH should be controlled between 6.5 and 8.5, or 6.8 and 7.2. Lower pH values do not immediately kill bacteria, but slowly starve it because it cannot acquire energy by metabolizing sugars from dissolved cellulose. Dissolution of the cellulose also stops because the products are not being metabolized.

In an example, the pH of the ASB tank 208 is controlled. In an example, a base is introduced for pH control and promotion of metabolism. In another example, a sufficient base is maintained to react with acids produced during metabolism. In another example, bicarbonate (e.g., $HCO_3$—, etc.) is introduced or recycled from at least one of the AD tank 208 and other environments described herein to control pH of the ASB tank 208. Metabolism and growth of *C. bescii* are driven by production of $CO_2$ gas or water. A base that does not produce sufficient Gibbs energy upon reaction with acids will not provide the energy required for optimum growth of the bacteria. Thus, an example includes that the base have a sufficient Gibbs energy to provide the energy needed for optimum growth.

Another condition for the ASB tank 208 is the alkalinity, or the amount of base to resist changes in pH that would make the contents more acidic. The base to be controlled within the ASB tank 208 may include carbonate and bicarbonate. In an example, bicarbonate is produced by the AD tank 212 and recycled to the ASB tank 208 to maintain a desired alkalinity or range of alkalinity.

*C. bescii* is believed to not form a biofilm on biomass particles. Instead, it produces a secretome with exozymes that catalyze dissolution of the lignocellulosic materials. In an example, the ASB tank 208 mixes the contents for *C. bescii* to increase contact between bacteria and biomass and support the production of exozymes that dissolve the lignocellulosic materials. An example mixing system includes a slow or low-level mechanical stirring or other suitable system for mixing. Means for mixing the contents may include one or more of a plurality of paddles and pumps 246.

ASB treatment examples include at least one of a batch process, semi-continuous process, and a continuous process. The reaction in the ASB tank 208 may depend on the time period depending on the feedstock and desired level of material destruction. In an example, ASB containment for reaction includes a period of time between 0 to 48 hours. In another example, the period of time is 0 to 7 days. The time for a reaction using *C. bescii* may be between 0.5 hour to 200 hours, but more typically 12-72 hours. *C. bescii* is suitable because it can rapidly depolymerize and solubilize lignocellulosic (plant material) and other cellular material. *C. bescii* further produces exozymes that catalyze hydrolysis of cellulose and lignin at a rapid rate. In an example, the products are sugars and phenolic compounds from lignin that are metabolized to acetic acid and lactic acid by *C. bescii* as a source of Gibbs energy for growth and activity.

In an example, at least a portion of the treated biomass and a portion of the biomass products are provided to the AD tank 212. To meet the conditions of the AD tank 212, the ASB effluent 210 may be cooled, for example, by a cooling reservoir or heat exchange system, prior to entering the AD tank 212 or other location.

ASB Treatment Reactions with *C. bescii* Include:

Lignocellulose→(acetate+lactate) ions+$CO_2$(g)+oxygenated aromatics from lignin+residual sugars. These reactions are catalyzed by exozymes produced by *C. bescii*. During treatment in the ASB tank 208, acetic and lactic acids in the presence of bicarbonate react to produce acetate ion, lactate ion, and $CO_2$ gas. Acetic and lactic acids react with base in the pH buffer to produce acetate ion, lactate ion, and $CO_2$ gas. The rate of ASB treatment can be obtained by monitoring the increase in $CO_2$ gas pressure over the ASB treatment mixture in a sealed vessel or by one or more of measurement of the change in total suspended solids and volatile solids as ASB treatment progresses. Products are not toxic to anaerobic digestion microorganisms and are rapidly digested in the AD tank 208 to produce biogas.

ASB Treatment Metabolic Reactions Include:

Sugars→acetic acid+lactic acid. For this reaction to occur at a significant rate, the concentration of acetic and lactic acid must be kept low by reaction with bicarbonate or another base.

Acetic acid+bicarbonate→acetate ion+$CO_2$+$H_2O$. The Acetate/Lactate ions and residual sugars are rapidly metabolized in the AD by anaerobic bacteria, producing $CO_2$, and $CH_4$, as follows;

Acetate/Lactate ions+sugars→methane+$CO_2$+bicarbonate (which may be recycled back to the ASB tank 208).

At least one bacterial organism used in the ASB tank 208 can be introduced by any suitable method, and conditions should be maintained for optimum growth. For example, trace elements, nutrients, vitamins, and the like may be introduced to start or maintain the ASB treatment process.

For *C. bescii*, specific optimum conditions have been shown to include the following: 78° C., DSMZ media (0.33 g $NH_4Cl$, 0.33 g $KH_2PO_4$, 0.33 g KCl, 0.33 g $MgCl_2*6H_2O$, 0.33 g $CaCl_2)*2H_2O$, 0.50 g Yeast Extract, 0.50 mL Na-resazurin solution (0.1% w/v), 1.50 g $NaHCO_3$, 0.50 g $Na_2S*9H_2O$, 1.00 mL of a trace element solution, 10.00 mL of a vitamin solution to 1000.00 mL distilled water.

The trace element solution (designated SL-10) was, in an example, composed of 10.00 mL HCl (25%; 7.7 M), 1.50 g $FeCl_2*4H_2O$, 70.00 mg $ZnCL_2$, 100.00 mg $MnCl_2*4H_2O$, 6.00 mg $H_3BO_3$, 190.00 mg $CoCl_2*6H_2O$, 2.00 mg $CuCl_2*2H_2O$, 24.00 mg $NiCl_2*6\ H_2O$, 36.00 mg $Na_2MoO_4*2\ H_2O$, and 990.00 mL Distilled water. The $FeCl_2$ was dissolved in the HCl, which was then diluted in water. The remaining salts were added and the solution was diluted to 1000.0 mL. The vitamin solution was composed of 2.00 mg Biotin, 2.00 mg Folic acid, 10.00 mg Pyridoxine-HCl, 5.00 mg Thiamine-HCL*2H20, 5.00 mg Riboflavin, 5.00 mg Nicotinic acid, 5.00 mg D-Ca-pantothenate, 0.10 mg Vitamin B12, 5.00 mg Lipoic Acid, and 1000.00 mL Distilled water. The solutions should be stored under anaerobic conditions.

In prior art processes, a great expense may be involved in hauling away and safely disposing of waste material. The ASB tank 208 and other components described herein have great market potential because of the increase in quantity of commercially viable product that they yield over current methods. This reduces undigested waste material.

Another advantage in using the ASB tank 208 and other components is that they yield 1.5 to 10 times as much gas than if biomass is put directly into an AD tank 212.

AD Tank

After the ASB tank 208, at least a portion of the ASB treated biomass 210 enters the AD tank 212. Compared to conventional feed streams of an anaerobic digester, the ASB treated biomass 210 is more available for anaerobic metabolism and digestion than typical biomass feeds to anaerobic digestion. In particular, an advantage of extremely thermophilic ASB treatment is its pasteurization of the biomass 209 before being introduced into the AD tank 212, thus allowing better control of the AD microbes and processing.

For acetate only ASB effluent 210, $CO_2$ may still be present in the biogas from digestion within the AD tank 212. It is speculated that such $CO_2$ in the biogas may come from compounds other than acetate that were produced in the ASB tank 208.

Within the AD tank 212 are maintained suitable bacteria and archaea, such as acetogens and methanogens, that support production of biogas. Methanogens grow better with the ASB treated biomass 210 from the ASB tank 208 than with conventional untreated biomass. In an example, the AD tank 212 includes at least one of anaerobic bacteria and archaea to convert the treated biomass 210 into biogas under anaerobic digestive conditions. In another example, a portion of the AD treated biomass 211 is recycled back to the ASB tank 208 as indicated by the black arrow. The portion of AD treated biomass 211 may include, for example, basic bicarbonate or other bicarbonate produced within the AD tank 212 that may be recycled to control pH and promote metabolism with the ASB tank 208.

In other examples, at least one of the AD tank 212 and an AD satellite reservoir 236 provides the basic bicarbonate or other bicarbonate to the ASB tank 208. In an example, the bicarbonate is taken after AD treatment and can be a specified amount as needed or desired. In an example, the AD tank 212 is preferred for drawing bicarbonate with the AD satellite reservoir 236 being a back up resource.

Conditions in the AD tank 212 are maintained to allow anaerobic bacteria to thrive. An example temperature includes 40° C. Further examples include a temperature range between 15° C. to 85° C. The pH of the AD tank 212 may range from 6.5 to 8.5, with more narrow ranges including 6.5-7, 7-7.5, 7.5-8, or 8-8.5. In an example, the pH of the AD tank 212 is maintained at 7 or slightly below 7 (e.g., 6.5-6.6, 6.6-6.7, 6.7-6.8, 6.8-6.9, 6.9-7, etc.). In another example, the temperature and pH are substantially different from the temperature and pH in the ASB tank 208. Maintaining disparate conditions where an organism of the ASB tank 208 and the bacteria in the AD tank 212 can thrive is at least one reason that separate tanks or digesters are provided for each part of the treatment.

The AD tank 212 may include at least one of a continuous stir, up flow anaerobic sludge blanket, induced bed reactor, dual anaerobic/aerobic digester, or any kind of anaerobic digester for the reaction. Treatment may be at least one of a batch process, semi-continuous process, and a continuous process.

In an example, the ASB tank 208 has a volume ratio with the AD tank 212 between 1:10 to 10:1 as defined by a relative rate of degradation of the biomass in the ASB tank 208 to the production of biogas in the AD tank 212.

In an example, the AD tank 212 has two main product streams including principally gas and liquid phase streams. The first main output stream (1), or biogas stream, contains at least one of methane ($CH_4$) and carbon dioxide ($CO_2$), but may also contain other reaction products and impurities (e.g., $H_2S$, and $H_2O$). The biogas stream is directed to suitable gas processing for its intended use. Bicarbonate is recycled back to the ASB tank 208. The second main output stream (2) is a slurry of undigested waste (dead bacteria, inorganic portions, dirt, etc.) that has been pasteurized, and which therefore can be processed as a soil conditioner or compost. In an example, there is no biomass left. Because the biogas stream is considered to be pathogen free, pasteurization produces a higher quality, more valuable undigested waste than conventional AD treatment.

Reactions in the AD Tank Include:

$$CH_3COO^-_{(aq)} \rightarrow CH_{4(g)} + HCO_3^-_{(aq)} \quad \text{(Acetate)}$$

$$2CH_3CH(OH)COO^-_{(aq)} + H_2O \rightarrow 3CH_{4(g)} + 2HCO_3^-_{(aq)} + CO_{2(g)} \quad \text{(Lactate)}$$

$$2C_1H_2O \rightarrow CH_{4(g)} + CO_{2(g)}, \quad \text{(Sugars)}$$

Production of acetate in the ASB tank 208 uses one bicarbonate and digestion of acetate produces one bicarbonate in the AD tank 212. Production of lactate uses one bicarbonate and digestion of lactate produces one bicarbonate ion. Thus, the reactions in the AD tank 212 produce the same amount of bicarbonate as the amount used in treatment in the ASB tank 208. Balancing bicarbonate (i.e. acid/base balance) would require recycling 100% of the biomass effluent from the AD tank 212. Efficiency of that nature is unlikely to be possible and not practical. Instead, bicarbonate may be introduced to the ASB tank 208 or the mixing tank 202 from other sources, or by adding another base to the ASB tank, such as ammonia, sodium carbonate, sodium bicarbonate, potassium hydroxide, and sodium hydroxide.

An application of ASB/AD digestion system will include optional systems designed to exploit the advantages of the ASB/AD system, and provide a suitable industrial operating environment. Below is a fuller description of exemplary systems.

Treating biomass with the ASB prior to anaerobic digestion is effective in promoting anaerobic digestion and does not introduce any harmful chemicals or otherwise harm the environment for the anaerobic bacteria in the AD tank 212 where biogas is produced. Note that *C. bescii* and other thermophiles are not considered to be pathogens because they cannot survive at low or mesophilic temperatures.

Mixing Tank

A mixing tank may be used to treat biomass before entering the ASB tank 212. The mixing tank 202 includes treatment that is to create a feedstock, or biomass effluent 209, for the ASB tank 212 that is suitable for and that promotes growth of the thermophilic microbes of the ASB tank 208. The mixing tank 202 may mix biomass with water, and possibly other reagents as well. In addition, the mixing tank 202 may heat the biomass 258. Mixing the biomass 258, or mixing and heating of the biomass 258 with water, may occur before treating the biomass 258 in the ASB tank 208 to mitigate pH changes and promote metabolism. Also, the mixing tank 202 may be used to remove oxygen from the biomass 258 and promote hydrolysis of biomass solids. In an example, the mixing and heating occurs prior to entry to the mixing tank 202.

Contents introduced to the mixing tank 202 having lignocellulosic biomass may include the same types of materials that enter the ASB tank 208, namely, at least one of animal waste (e.g., manure, etc.); human waste (e.g., biosolids, etc.); fats, oils, and grease (FOG); food waste/garbage; organic matter; plant matter (e.g., green waste, bio-energy crops, coconut husk, grass, etc.); waste activated sludge (WAS); and algae (e.g., algae grown in reactors, etc.), as well as other contents. Lignocellulosic biomass along with other types of raw material or feedstock may be introduced into the mixing tank being premixed together or added separately. Besides lignocellulosic biomass, biomass 258 contents may include non-lignocellulose biomass and waste paper that does not have lignin, such as slaughterhouse waste and waste paper.

Once the biomass 258 is treated with at least one of water, heat, and mixing, etc., the biomass effluent 209 from the mixing tank 202 is a treated biomass for the ASB tank 208 rather than its original form of biomass 258.

An example treatment includes the biomass 258 being ground to a 3 cm particle size and then being supplied to the mixing tank 202 before being introduced to the ASB tank 208. The contents of the mixing tank 202 are adjusted to a composition that is approximately 2% to 50% (e.g., 6% has been found suitable), and heated to approximately 60° C. to 100° C. for 1 to 6 hours. During this period of time, mixing can be accomplished, for example, with one or more of a plurality of paddles 244 and/or pumps. This process has the effect of pasteurizing the contents, expelling dissolved $O_2$, and providing the contents with an optimal temperature for thermophilic microbial action.

The resultant biomass effluent 209 produced by the mixing tank 202 is sent to the ASB tank 208 in the form of a liquid suspension, slurry, or mash of solids. An example solids content of the effluent may represent approximately 10% of the effluent.

In an example, a solution or "tea" containing soluble materials in the biomass 258 or treated biomass 209 is separated from the solids content and sent directly to an AD tank 212. In another example, the biomass 258 is mixed with water to suspend at least a portion of the biomass 258 in the water and partially solubilize components of the biomass 258. In another example, the biomass effluent 209 includes at least a portion of one of suspended biomass and partially solubilized components of biomass being transferred to the ASB tank 208.

For some types of biomass, raw material, and feedstocks, the mixing tank 202 can also serve as a hydration tank in which hydration is provided. Also, two separate tanks are contemplated, one tank for hydration and one tank for mixing.

ASB Satellite Reservoir

Satellite reservoirs may be provided that are associated with at least one of the tanks or environments, according to principles discussed herein. In an example, the ASB tank 208 benefits from a connection to a separate, independent ASB satellite reservoir 236. For example, there may be times when the ASB tank 208 becomes compromised due to a reinoculation failure. There may also be a bacterial, cultural, enoculum washout in which there is too short of a mean resonance time which pushes material out before bacteria grows. As a result, the whole community becomes washed out because the bacteria cannot grow fast enough. In another example, toxins and antibiotics in the biomass are present. There may also be a chemical restrictions of the feedstock presented, or other problem. To counter occurrences of this nature and prevent failure of the ASB tank 208, an ASB satellite reservoir 236 as shown in FIG. 1 efficiently maintains and provides at least one of a bacteria, nutrient, or other matter to the ASB tank 208 as needed or desired to promote digestion of the biomass effluent 209. The satellite reservoir 236 may be provided with an environment to, for example, provide inoculation, assist in maintaining a condition, assist in startup, or introduce/maintain a precultured microbe culture, a chemical agent, micronutrient, or the like. Any storage or auxiliary processing that can be maintained separately from the main environment and that enhances the main environment is contemplated. Satellite reservoirs can be particularly useful when applied to an ASB environment and an AD environment.

In addition, the ASB satellite reservoir 236 may also be used for at least one of the following—1) maintaining bacteria culture suited for the ASB tank 208, 2) alleviating the need for trace elements to be added to the ASB tank 208, depending on feedstock chemical characteristics, 3) adapting or conditioning *C. bescii* to utilize the feedstock present in the ASB tank 208, 4) speeding up the ASB treatment process in the ASB tank 208 by avoiding time that otherwise would be required for the *C. bescii* to grow in the ASB tank 208, and 5) adding a base, such as bicarbonate, to the ASB tank 208 to maintain pH and support metabolism.

In an example, the ASB satellite reservoir 236 facilitates the continuous inoculum of *C. bescii*. In addition, the satellite reservoir 236 contains nutrients necessary for *C. bescii* growth and a small amount of the ASB treatment feedstock (e.g., biosolids, green waste, energy crops, food waste, raw or organic materials, etc.). The *C. bescii* or other matter in the satellite reservoir is maintained at or near $1 \times 10^6$ cells per milliliter density.

Bacteria besides *C. bescii* that may be maintained in the ASB satellite reservoir 236 includes one or more of *Caldicellulosiruptor bescii*, *Caldicellulosiruptor* genus, *Clostridium thermocellum*, *Thermoanaerobacterium saccharolyticum*. Note that bacteria in the ASB satellite reservoir 236 is maintained at a pH range of 6.5-7, 7-7.5, 7.5-8, 8-8.5, 6.5-7.5, 7.5-8.5, or 6.5-8.5. Additionally, the bacteria may be cultured separately before being added to the ASB satellite reservoir 236.

In an example, the ASB satellite reservoir 236 maintains at least one of bacteria and archaea to be fed to the ASB tank 208. The ASB satellite reservoir 236 may maintain at least one of the following—a nutrient for bacterial growth, food waste, animal manure, biosolids, waste organic material, sewage, garbage, waste activated sludge, FOG, waste paper, lignocellulosic plant materials, and cellular material.

In addition to bacteria and nutrients, at least one of a trace nutrient and trace element may be maintained in the ASB satellite reservoir 236. In an example, at least one of a trace nutrient and trace element are maintained that is necessary for a bacteria in the ASB tank 208 to grow and divide. In another example, at least one of a trace nutrient and trace element are maintained to overcome a chemical restriction of the feedstock in the ASB tank 208. In operations that include *C. bescii*, at least one additional nutrient and trace metal may be provided to further facilitate *C. bescii* growth. Exemplary trace elements and proportionate amounts to obtain 1000 mL are shown in Table C below.

TABLE C

| Trace element solution SL-10: | |
| --- | --- |
| HCl (25%; 7.7M) | 10.00 ml |
| $FeCl_2 \times 4\ H_2O$ | 1.50 g |
| $ZnCl_2$ | 70.00 mg |
| $MnCl_2 \times 4\ H_2O$ | 100.00 mg |
| $H_3BO_3$ | 6.00 mg |
| $CoCl_2 \times 6\ H_2O$ | 190.00 mg |
| $CuCl_2 \times 2\ H_2O$ | 2.00 mg |
| $NiCl_2 \times 6\ H_2O$ | 24.00 mg |
| $Na_2MoO_4 \times 2\ H_2O$ | 36.00 mg |
| Distilled water | 990.00 ml |
| First dissolve $FeCl_2$ in the HCl, then dilute in water, add and dissolve the other salts. Finally make up to 1000.0 ml. | |

In addition, a sucrose or a carbon source may be maintained in the ASB satellite reactor 236 to promote optimal conditions for bacteria to grow and thrive and ultimately produce enzymes that will benefit the contents of the ASB tank 208. Also, a yeast, such as brewer's yeast, may be added to the ASB satellite reservoir 236 to promote growth of the bacteria by providing needed amino acids. An example sample of nutrients per liter maintained in the ASB satellite reservoir 236 include glucose (1 g), yeast extract (0.1 g) (e.g., brewer's yeast or another source of amino acids, etc.), $NH_4Cl$ (0.05 g), $KH_2PO_4$ (0.05 g), $MgCl_2$ (0.05 g), $CaCl_2$) (0.05 g), $NaHCO_3$ (1.0 g), and $Na_2S$ (0.1 g to ensure anaerobic conditions). Note that the ASB satellite reservoir 236 may provide one specific type of content or a combination of at least one of a bacteria, nutrient, trace nutrient, trace element, sucrose, carbon matter, and other matter.

In an example, the contents in the ASB satellite reservoir 236 are grown on a substrate or other contents that are the same or similar to the biomass in the ASB tank 208. For example, if the biomass within the ASB tank 208 contains manure, the contents within the ASB satellite reservoir 236 are grown on manure or contents that include manure. If sludge is in the biomass, sludge is used as the substrate or as part of the substrate within the ASB satellite reservoir 236.

The similar contents enable similar bacterial propagation between the two environments. If the contents in the ASB satellite reservoir 236 are only given one type of biomass, the contents will have a difficult time being able to break down foreign types of biomass that are present in the ASB tank 208. The reason for this is that bacteria will not make enzymes that are not needed. For example, growing bacteria with only sucrose in the ASB satellite reservoir 236 will shut down genes that are not needed to metabolize sucrose. Introducing the sucrose fed bacteria into an ASB tank 208 that contains grass clippings will make the bacteria unable to break down the grass clippings because the bacteria were conditioned to metabolize sucrose. Maintaining similar conditions of bacteria and biomass between the ASB tank 208 and the ASB satellite reservoir 236 is therefore a support to the system as a whole.

In an example, the substrate comprises at least one of biomass effluent 209 from the mixing tank 202, ASB effluent 210 from the ASB tank 208, AD treated biomass 240 from the AD tank 212, nutrient for growth, food waste, human waste, animal manure (animal waste), biosolids, waste organic material, sewage, garbage, waste activated sludge, algae, FOG, organic matter, plant matter, waste paper, lignocellulosic plant materials, and cellular material. In addition to the substrate, the ASB satellite reservoir 236 may contain, for example, at least one acetoclastic methanogen.

Additional conditions of the ASB satellite reservoir 236 may by close or identical to that of the ASB tank. In an example, oxygen levels within the ASB satellite reservoir 236 are the same as, or similar to, the oxygen levels as the ASB tank 206. In another example, the ASB satellite reservoir 236 is configured to adhere to the oxygen limits for *C. bescii*, based on *C. bescii* being a strict anaerobe, which is $pO_2=0.5\%$. The satellite reservoir 236 may further be configured for higher oxygen levels, such as $pO_2=2\%$ for 15-20 minutes. Maintaining a same oxygen level or maintaining certain oxygen levels for at least one or more specific constraint, such as a given set of contents and for certain time durations, may support the growth rates desired of the system.

Another condition of the ASB satellite reservoir 236 that may be close or identical to that of the ASB tank 206 is temperature. This may be a constraint that helps the ASB satellite reservoir 236 to stay inoculated with a particular bacteria that is suited for the ASB tank 206. Furthermore, maintaining a specific temperature or temperature range may enable the ASB satellite reservoir 236 to stay inoculated with a particular bacteria that is suited for the ASB tank 206. Temperature ranges that are maintained and that may be the same or similar to the temperature ranges of the ASB tank 206 may include, for example, 60-65° C., 65-70° C., 70-75° C., 75-80° C., 80-85° C., 60-70° C., 70-80° C., 70-85° C., or 60-85° C. degrees. Furthermore, temperature changes may be minimized during transport of contents from the ASB satellite reservoir 236 to the ASB tank 206 to protect the state of the bacteria or other matter.

Specific volume ratios or a range of volume ratios may also be observed between the ASB satellite reservoir 236 and the ASB tank 206. In an example, the satellite reservoir 236 has a volume ratio to the ASB tank 206 within a range of 1:10 to 10:1. In another example, the volume of the ASB satellite reservoir 236 is approximately 1/100 the volume of the ASB tank 206, or within a range of 1/200 to 1/2 of the volume of the ASB tank 206. In terms of mass per volume, the ASB satellite reservoir 236 may contain 0.5-1.0% of the ASB treated biomass. The volume ratios and percentages may be used to control and predict behavior of the contents within the ASB satellite reservoir 236 and the ASB tank 206.

In an example, the ASB satellite reservoir 236 provides at least one of a bacteria, nutrient, or other matter, primarily at two different times. The first time is at or near the beginning of the ASB treatment. The second time occurs when trace nutrients are depleted and not provided by the feedstock.

In another example, feeds to the ASB tank 206 occur at various times and in a manner so as to maintain an exponential growth culture. The mean doubling times for various feedstocks with *C. bescii* are shown in Table A1 below to provide information on the way to feed the ASB tank 206 so as to maintain their exponential growth culture. *C. bescii* growing on starch, for example, has a mean doubling time of 2.1 hours and therefore, quantities of the starch within the ASB tank 206 may be fed with contents in the ASB satellite reservoir 236 to double the amount of starch within that time frame.

TABLE A1

Feedstock and the mean doubling time with *C. bescii*

| Feedstock | *C. bescii* Mean Doubling Time (hours) |
|---|---|
| Starch | 2.1 |
| Newspaper | 4.6 |
| Barley Shoots | 3.6 |
| Kentucky Blue Grass lawn clippings | 3.4 |
| Switchgrass | 2.3 |
| Poplar twigs | 2.4 |
| Corn Husk | 4.3 |

If a feedstock lacks the necessary requirements for *C. bescii* growth, contents from the ASB satellite reservoir 236 may provide specific chemical constituents to maintain such growth. For example, the C:N:P ratio of 500:10:1 dictates the addition of major nutrients, N and P, as $NH_4Cl$, yeast extract, and/or $KH_2PO_4$.

An example ASB satellite reservoir 236 includes a monitoring system or device that monitors at least one of pH level, oxygen content, and type of bacteria present within the reactor. The monitoring system or a second monitoring system may further monitor at least one of the ASB tank 208 and AD tank 212. A delivery system manually, automatically, or semi-automatically delivers contents from the ASB satellite reservoir to the ASB tank 208 in quantities that are determined to be needed for the ASB tank 208. In an example, chemical analysis is performed so that trace metals that are lacking in the ASB tank 208 may be added including at least one of Fe, Zn, Mn, B, Co Cu, and Ni. In another example, product formation of acetate, lactate, oxygenated aromatic compounds, etc., is also monitored. The ASB satellite reservoir 236 may require that its entire volume be replaced every 72 hours or within a range of 50-80 hours.

AD Satellite Reservoir

Figure 2:
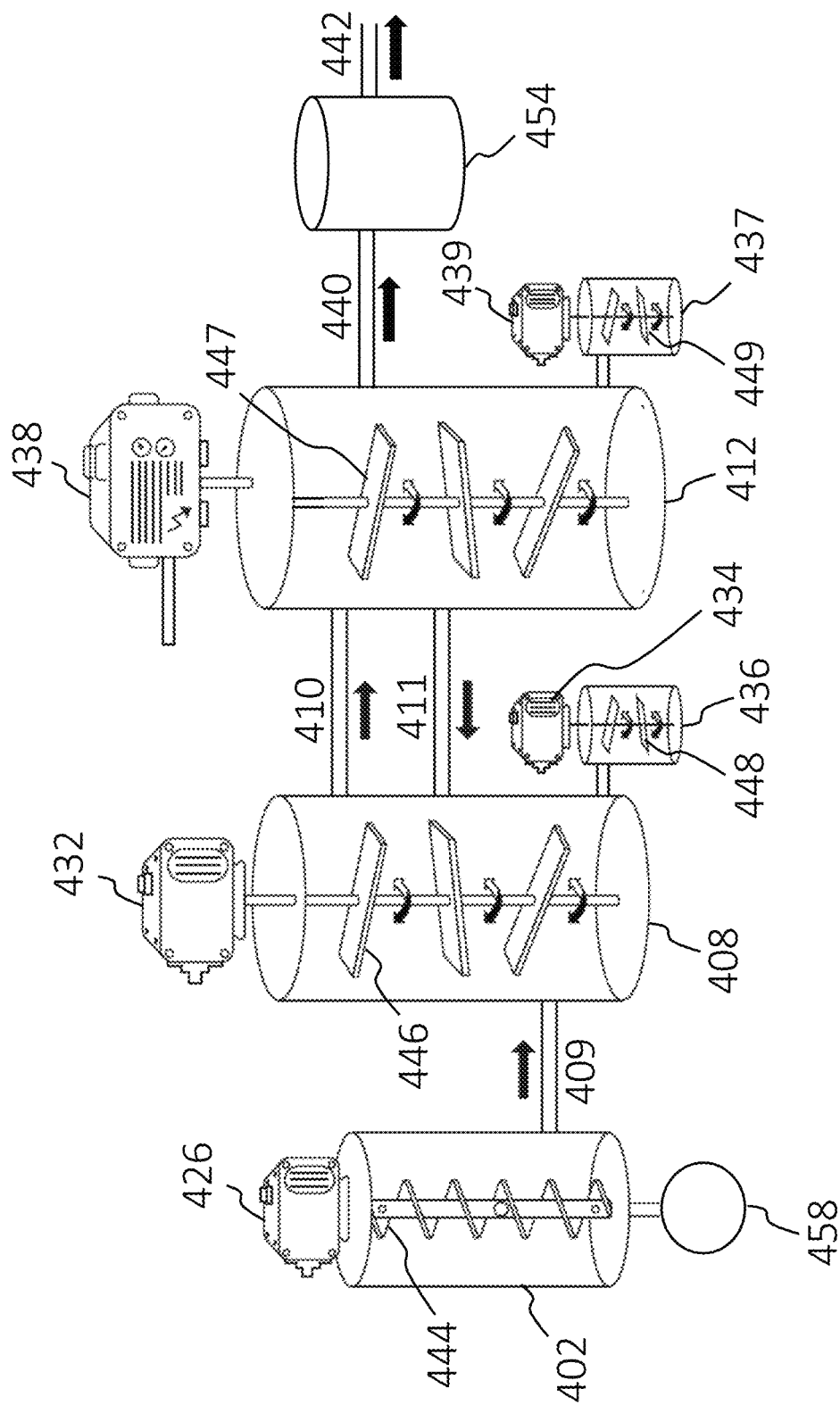
FIG. 2 illustrates a diagram of an example reactor according to principles described herein.

Like the ASB tank 206, a separate, independent satellite reservoir may be connected to the AD tank 212. This is shown in FIG. 2 in which an example reactor includes an AD satellite reservoir 437 attached to an AD tank 412. The rest of the reactor may remain the same as FIG. 1, with a mixing tank 202, ASB tank 208, ASB satellite reservoir 236, and various components therein.

In FIG. 2, biomass 458 is supplied to the mixing tank 402 for mixing by mixing paddles 444 as powered by mixing motor 426. Biomass effluent 409 that is produced in the mixing tank 402 is supplied as indicated by a black arrow to the ASB tank 408. ASB treatment within the ASB tank 408 may include mixing by mixing paddles 446 and heat. The ASB tank 408 may be powered by the ASB motor 432.

In an example, the ASB satellite reservoir 436 is used to supply one or more of a bacteria, nutrient, or other matter to the ASB tank 408. The contents within the ASB satellite reservoir 436 may be mixed by mixing paddles 448 and heated. The ASB satellite reservoir 436 may be powered by the ASB motor 434.

ASB treated biomass 410 that is produced by the ASB tank 408 is supplied to the AD tank 412, as indicated by a black arrow, for anaerobic digestion. The AD tank 412 includes mixing by mixing paddles 447 and heating capabilities to treat the contents therein, as powered by AD motor 438. In an example, at least a portion of the contents such as $CO_2$ and bicarbonate 411 that are produced within the AD tank 412 are recycled back to the ASB tank 408, as indicated by a black arrow, or used for other purposes.

The AD satellite reservoir 437 is used to supply additional contents to the AD tank 412. The contents within the AD satellite reservoir 437 may be mixed by mixing paddles 449 and heated. The AD satellite reservoir 437 may be powered by an AD satellite motor 439. In an example, the AD satellite reservoir 437 contains at least one of the contents found in the AD tank 412. In another example, the AD satellite reservoir 437 contains substantially similar or identical content as found in the AD tank 412. In another example, at least one of archaea, acetoclastic consortium, and other matter is provided to the AD tank 412. In an example, the AD satellite reservoir 437 incubates bacteria that is used to augment desired bacteria in the AD tank 412 for processing of the ASB treated biomass in the AD tank 412. In another example, the AD satellite reservoir 437 maintains at least one of bacteria and archaea that are used to augment at least one bacteria and archaea in the AD tank 412. In a further example, the AD tank 412 is augmented from the AD satellite reservoir 437 with at least one of archaea and acetoclastic consortium isolated from WAS. In another example, the AD satellite reservoir 437 augments bacteria in the AD tank 412 that are specific to biogas production from the molecules being produced in the ASB tank 408. In another example, the AD satellite reservoir 437 supplies one or more of a nutrient solution and base to the AD tank 412.

The AD tank 412 may contain at least one of a synthetic content or biogenetically engineered content which are bio-augmented. The AD satellite reservoir 437 may also contain respective synthetic contents or biogenetically engineered contents.

Bioaugmentation with archaea has shown a significant reduction of acetate accumulation within seven days and the proportion of methane in biogas increased almost over a hundred-fold (Town and Dumonceaux, 2015). In an example, at least one of archaea and acetoclastic consortium is isolated during multiple successful digestions of WAS when methane production is relatively high to increase the likelihood that the archaea will thrive within similar AD conditions. The archaea or acetoclastic consortium may be cultured with DSMZ Medium 141 to capture local methanogens and an additional consortium is created that is spiked with two well-known *Methanosarcina, Methanosarcina barkeri*, DSMZ 800, and *Methanosarcina acetivorans* DSMZ 2834.

Consortia may be cultivated continuously at 55° C. for 6 months prior to bioaugmentation experiments in the AD tank and produced with consistent levels of methane in biogas. In an example, at least one of archaea and acetoclastic consortium may be added to the AD tank by an AD satellite prior to WAS/AD and periodically to reseed the AD tank when methane production drops.

There may be multiple satellite reservoirs for one tank, either duplicate, or with a different content, depending upon the specific content or purpose. For example, there may be two satellite tanks associated with the ASB, one for micronutrients, and another for *C. bescii*. In another example, there may be three types of satellite reservoirs, including at least one to deliver the bacteria, at least one to provide nutrients, and at least one to provide microbes, such as thermophilic microbes (*C. bescii*) for the ASB or NT microbes from the AD. In another example, nutrients provided by a satellite reactor include at least two main types of contents, such as two types of nutrients or two types of trace metals. In another example, the satellite reactor provides a combination of types of contents, such as at least one type of nutrient and at least one type of trace metal.

An example of a reactor system includes at least three satellite reservoirs that supply contents to the ASB and AD tanks, each satellite reservoir providing same or different contents at same or different times and rates. The first satellite reservoir is for the ASB tank and includes *C. bescii*, the second satellite reservoir is for the AD tank and includes at least one of archaea and acetoclastic bacteria, and the third satellite reservoir for the AD tank includes oxidative methanogenic bacteria. In another example, a specific type of bacteria, either the archaea, acetoclastic bacteria, or the oxidative bacteria, is delivered to the AD tank. In another example, predetermined quantities of bacteria from each tank are delivered to the AD tank. Further examples include that controls over at least one of an amount, time, or rate depends on determinations made by a monitoring process or other process.

In an example, the AD satellite reservoir contains bacteria grown on a substrate that is close or identical to effluent from the ASB tank. The contents may be grown on a substrate or other contents that are close or identical to the biomass effluent 409 in the ASB tank 408. In an example, the substrate comprises at least one of biomass effluent 409 received from the ASB tank 408, nutrient for growth, food waste, human waste, animal manure (animal waste), biosolids, waste organic material, sewage, garbage, WAS, algae, FOG, organic matter, plant matter, waste paper, lignocellulosic plant materials, and cellular material. In addition to the substrate, the AD satellite reservoir 437 may contain, for example, at least one of acetoclastic methanogen and archaea.

At least one condition of the AD satellite reservoir 437 may be close or identical to at least one of the AD tank 412 or other environment. Such conditions may include, for example, oxygen levels, temperature, volume ratios, and ranges thereof.

Maintaining a specific temperature or temperature range may enable the AD satellite reservoir 437 to stay inoculated with a particular bacteria that is suited for the AD tank 412. Temperature ranges that are maintained and that may be the same or similar to the temperature ranges of the AD tank 412 may include, for example, 60-65° C., 65-70° C., 70-75° C., 75-80° C., 80-85° C., 60-70° C., 70-80° C., 70-85° C., or 60-85° C. degrees. Furthermore, temperature changes may be minimized during transport of contents from the satellite reservoir to the AD tank 412 to protect the state of the contents.

The same or similar type of monitoring processes as the AD tank 412 may be implemented with the AD satellite reservoir 437, whether the monitoring be the same system or a separate, independent system.

In an example, the AD satellite reservoir 437 has a volume ratio to the AD tank 412 within a range of 1:10 to 10:1 as defined by a relative rate of degradation of the biomass in the ASB tank 408 to the production of biogas in the AD tank 412. In another example, the volume of the AD satellite reservoir 437 is approximately $\frac{1}{100}$ or within a range of $\frac{1}{200}$ to $\frac{1}{2}$ of the volume of the AD tank 412. The volume ratios and percentages may be used to control and predict behavior of the contents within the AD satellite reservoir 437 and the AD tank 412.

Although reference is made specifically to the AD tank 412, the AD satellite reservoir 437 may supply contents to other environments and its principles may be applicable to other tanks and processes described herein and are not intended to be limited to the AD tank 412.

Applying these findings, a synthetic microbial community may be incorporated in at least one of the ASB tank 408 and in the AD tank 412. A synthetic microbial community is a systems approach to reducing the complexity, while increasing the controllability, by selecting genetically-engineered or wild type microorganisms that cooperate metabolically. The combination of different microbial species may decrease the potential competition between species, often leading to the co-metabolism of a substrate in an independent manner. In the ASB tank 408, for example, depending on feedstock, an additional species, such as *Clostridium thermocellum*, may be provided by the ASB satellite reservoir 436 or AD satellite reservoir 437 to help decompose difficult to digest biomass (e.g., lignocellulolytic materials). Also, a synthetic community of substrate dependent microbes configured specifically to digest acetate and lactate and the products of ASB treatment may be provided by the AD satellite reservoir 437.

In an example, the ASB tank 408 favors production of acetate ion over lactate ion to produce a reduced $CO_2$ content in the biogas from the AD tank 412 and to produce increased bicarbonate which may be used in at least one of the ASB tank 408 and AD tank 412. Please see Section A entitled EXAMPLE KINETIC MODEL to see a model that shows that ASB treatment results in ASB effluent with acetate as the major ASB treatment product.

Biogas Processing

If desired, at least a portion of AD biogas produced in an AD tank may be used by itself or be subjected to a at least one of a biogas processor or conditioner to process or condition biogas suitable for its intended use. The biogas processor may remove at least one of siloxanes, carbon dioxide, hydrogen sulphide, moisture (e.g., water, etc.), and contaminants from the AD biogas to make it suitable for at least one intended use. Further processing is also anticipated with the biogas conditioner.

Figure 3:
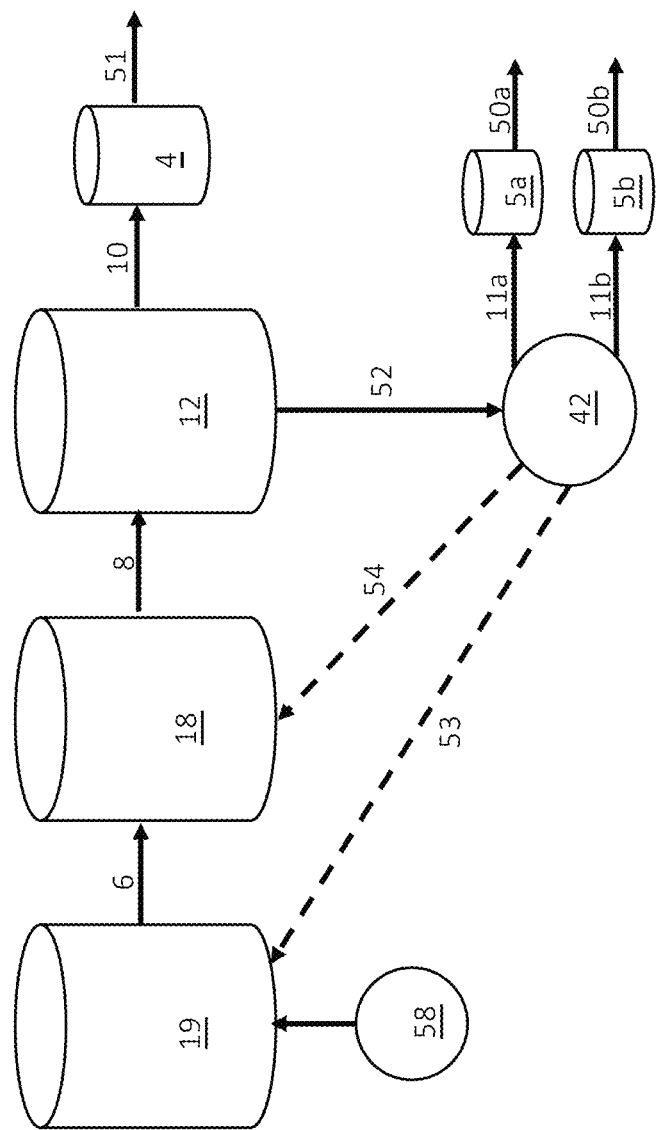
FIG. 3 illustrates a diagram of an example reactor according to principles described herein.

Turning to FIG. 3, a reactor is shown that includes the use of a biogas processor 42 used in conjunction with a mixing tank 19, ASB tank 18, and AD tank 12. As in previous examples, at least a portion of the AD biogas 10 goes through a gas processor 4 to be processed. This may involve the removal of components of the gas or at least one or more chemical reactions with the AD biogas 10. In a further example, at least a portion of the AD biogas 52 goes through a biogas processor 42 with a more purified gas form resulting. The more purified gas form may be directed to at least one of a pipeline and an electrical generator. This is demonstrated as shown by purified gas form 11*a* entering a gas processor 5*a* to yield methane 50*a*, and purified gas form 11*b* entering an electrical generator 5*b* to produce electricity 50*b*. Note that an example includes that the gas processor 4 may not be used if a biogas conditioner 42 is present.

In another example, at least a portion of the contents within the biogas processor 42 are recycled back or directed back to at least one of the mixing tank 19, ASB tank 18, or any other process tank or environment. Recyling lines are showed as dashed lines. The contents may include at least a portion of the more purified gas form or at least one specific content that is separated from the more purified gas form. As shown, contents 53 and 54 are directed to respective mixing tank 19 and the ASB tank 18. Specific contents separated from the more purified gas form may include, for example, at least one of $CH_4$ and $CO_2$ or other content that is used to aid its respective tank in processing its biomass content, as shown, biomass 58 treated within the mixing tank 19 and biomass effluent 6 treated within the ASB tank 18.

In another example, $CO_2$ is recycled to one or more of the mixing tank 19 or ASB tank 18. Gas processing requirements may be significantly reduced or eliminated by choice of the ASB bacteria and the processing conditions. As noted elsewhere, lactate in the AD tank 12 is metabolized to methane ($CH_4$), bicarbonate ($HCO_3^-$), and carbon dioxide ($CO_2$). Acetate is metabolized to methane and bicarbonate. Sugars are metabolized to methane and carbon dioxide. If carbon dioxide is reduced or eliminated as an AD tank product, gas processing to remove carbon dioxide can be correspondingly reduced or eliminated.

An experiment was conducted to test the modification of the bacteria and/or conditions in the ASB tank for production of only acetate instead of a mixture of acetate, lactate, and sugars. In an example, acetate is the feed, and may be the only feed, to the AD tank 12, such that modification of the AD bacteria and/or conditions enable the production of methane with little or no $CO_2$ in the AD biogas. This eliminates gas processing to remove $CO_2$, which is a costly process. In an example, at least one of a majority of acetate or only acetate is produced by ASB treatment with *C. bescii*.

In an example, the biogas is used to produce power generation. This involves combustion of the $CH_4$. The combustion gas, which contains mostly nitrogen, but also $CO_2$, may also advantageously be recycled to the mixing tank 19 or the ASB tank 18 to displace oxygen or air.

In another example, the biogas is processed and compressed for compressed natural gas (CNG). It may also be used as a feed stock for chemical processing, such as a Fischer-Tropsch process for production of biodiesel or other fuel.

Recycling, Heat Recovery, Purification

Figure 4:
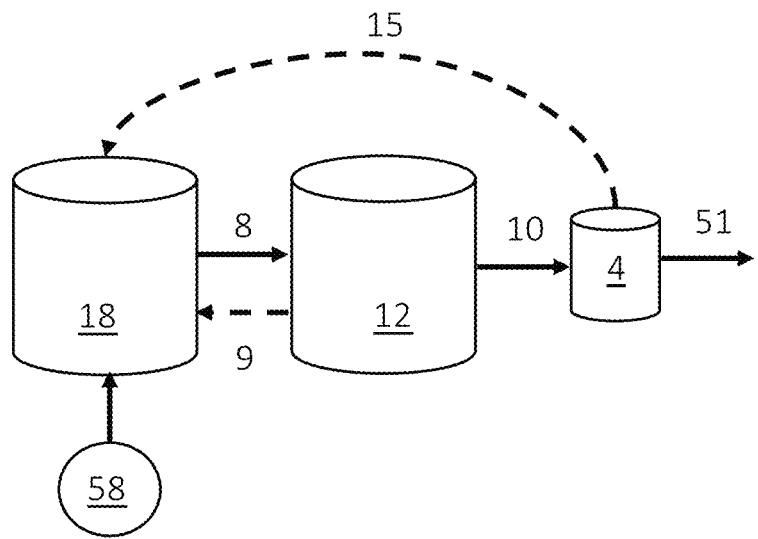
FIG. 4 illustrates a diagram of an example reactor according to principles described herein.
Figure 5:
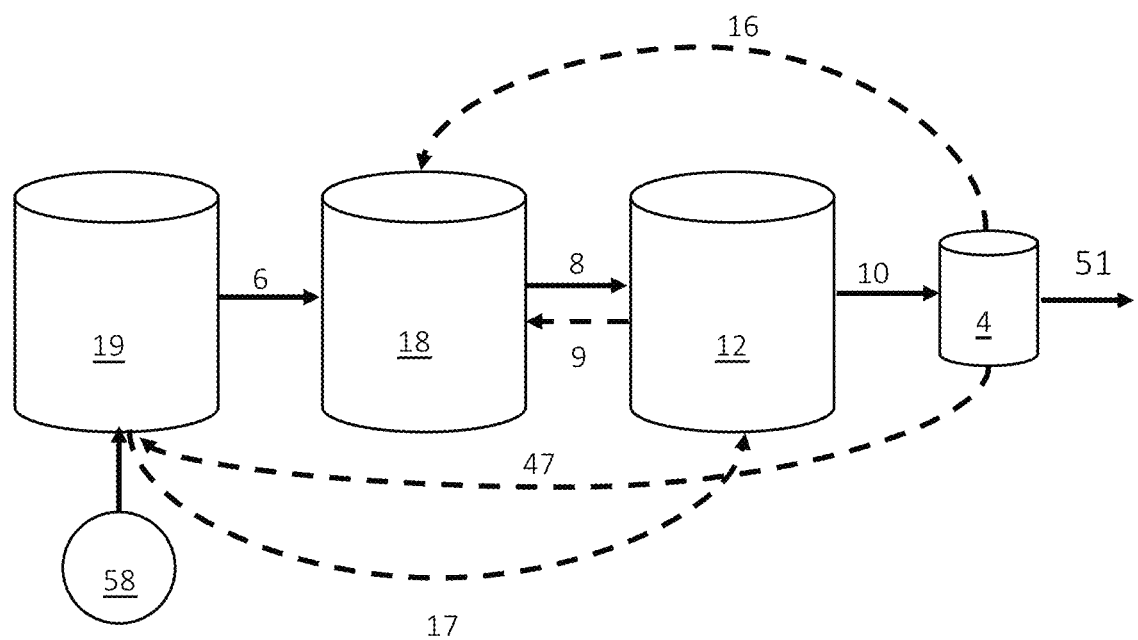
FIG. 5 illustrates a diagram of an example reactor according to principles described herein.
Figure 6:
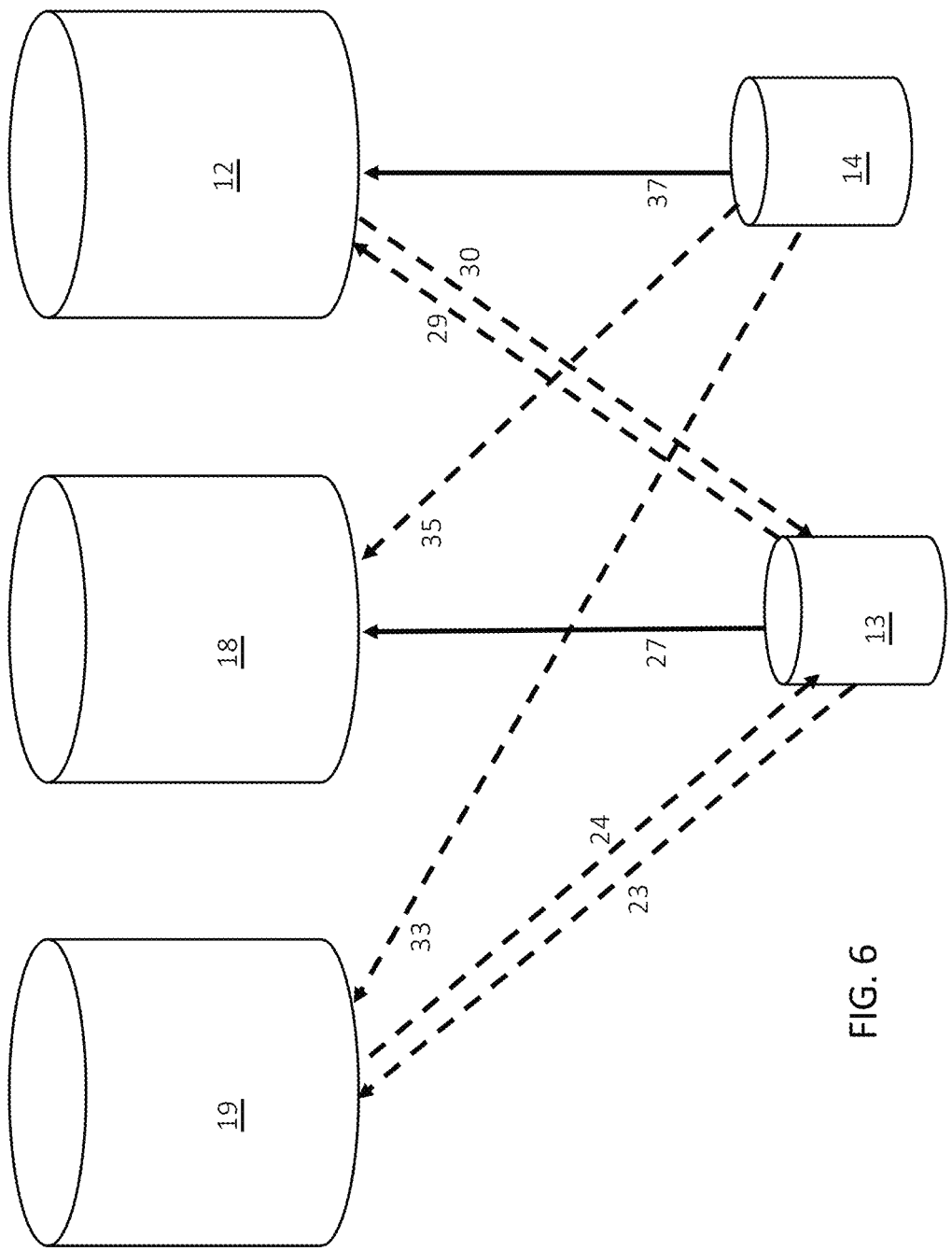
FIG. 6 illustrates a diagram of an example reactor according to principles described herein.

To increase process efficiency, reduce material costs, and reduce parasitic losses of material and energy, at least one of heat recovery, recycling, and purification can be employed. In an example, recycling streams may be implemented such that at least one environment provides at least a portion of its contents to at least one other environment before, during, or after a digestion related process occurs in that environment. Turning to FIGS. 4-6, black arrows show various paths in which content may flow and which may be used to promote at least one instance of recycling between at least one environment to at least another environment.

FIG. 4 illustrates recycling that may occur within a reactor that includes an ASB tank 18, AD tank 12, and biogas processor 4. Recycling lines are showed as dashed lines. As can be seen, content flow or recycling may occur in at least one of the following ways— biogas processor 4 to ASB tank 18 indicated by dashed line 15

AD tank 12 to ASB tank 18 indicated by dashed line 9

FIG. 5 illustrates recycling that may occur within a reactor that includes a mixing tank 19, an ASB tank 18, and AD tank 12 in at least one of the following ways— biogas processor 4 to ASB tank 18 indicated by dashed line 16

AD tank 12 to ASB tank 18 indicated by dashed line 9 mixing tank 19 to AD tank 12 indicated by dashed line 17 biogas processor 4 to mixing tank 19 indicated by dashed line 47

FIG. 6 illustrates content flow (lines 37 and 27) and recycling available with an ASB satellite reservoir 13 and an AD satellite reservoir 14. Recycling lines are showed as dashed lines. Content flow and recycling may include at least one of the following paths— the ASB satellite reservoir 13 to (dashed line 23) and from (dashed line 24) the mixing tank 19, the ASB satellite reservoir 13 to (dashed line 33) the ASB tank 18, the ASB satellite reservoir to 13 to (dashed line 29) and from (dashed line 30) the AD tank 12, the AD satellite reservoir 14 to (dashed line 33) the mixing tank 19 the AD satellite reservoir 14 to (dashed line 35) the ASB tank 18

Figure 7:
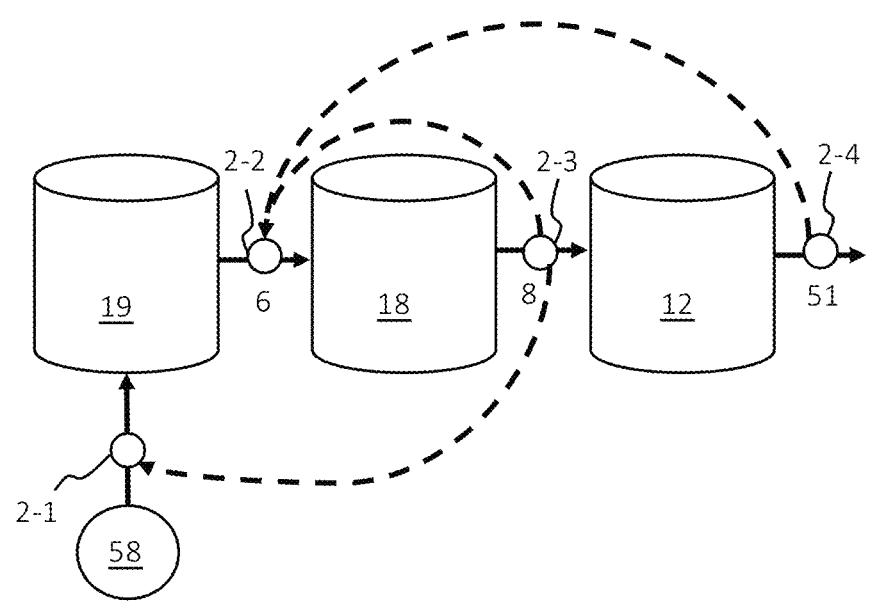
FIG. 7 illustrates a diagram of an example reactor according to principles described herein.

FIG. 7 illustrates various conduits used to recycle heat from the contents. Conduits are represented as circles and dashed lines. For example, conduit 2-4 to 2-2 recycles heat from the AD treated biomass 51 from the AD tank 12 to the biomass effluent 6 leaving the mixing tank 19. In another example, conduit 2-3 to 2-2 recycles heat from the ASB treated biomass 8 from the ASB tank 18 to the biomass effluent 6 leaving the mixing tank 19. In another example, conduit 2-3 to 2-1 recycles heat from the ASB treated biomass 8 from the ASB tank 18 to the biomass 58 that enters the mixing tank 19.

An example includes that heat be recycled to heat at least one of the tanks. Also, a heat exchanger may be used to heat the contents being recycled from at least one environment to at least one other environment. For example, a heat exchanger may heat the contents from the AD tank 12 to the ASB tank 18. Solar energy may also be used to heat contents from one environment to the other environment. For example, solar energy may be used to heat the contents from the AD tank 12 to the ASB tank 18.

Heat recovery may be significant. Recycling heat back to the ASB tank 18 or mixing tank 19 may help maintain respective temperatures. With an ASB tank 18 that is thermophilic, for example, at a temperature of about 75° C. and an AD tank 12 that is non-thermophilic, for example, at a temperature of about 40° C., the heat directed to the ASB tank 18 may be significant. In addition to recycling heat to an environment, heat recovery systems may be implemented to power another environment.

In addition to recycling and heating, example reactors may include purification treatments. For example, biomass 58 or biomass effluent 6 may first go through a purification processing treatment before being treated within the ASB tank 18. Separation and purification of the treated biomass 58 from the ASB tank 18 can occur, for example, by one or more of semi-permeable membranes, centrifuge purification, distillation, filtration, industrial chromatography with zeolites, sorption, and other known mechanical and chemical means.

Figure 8:
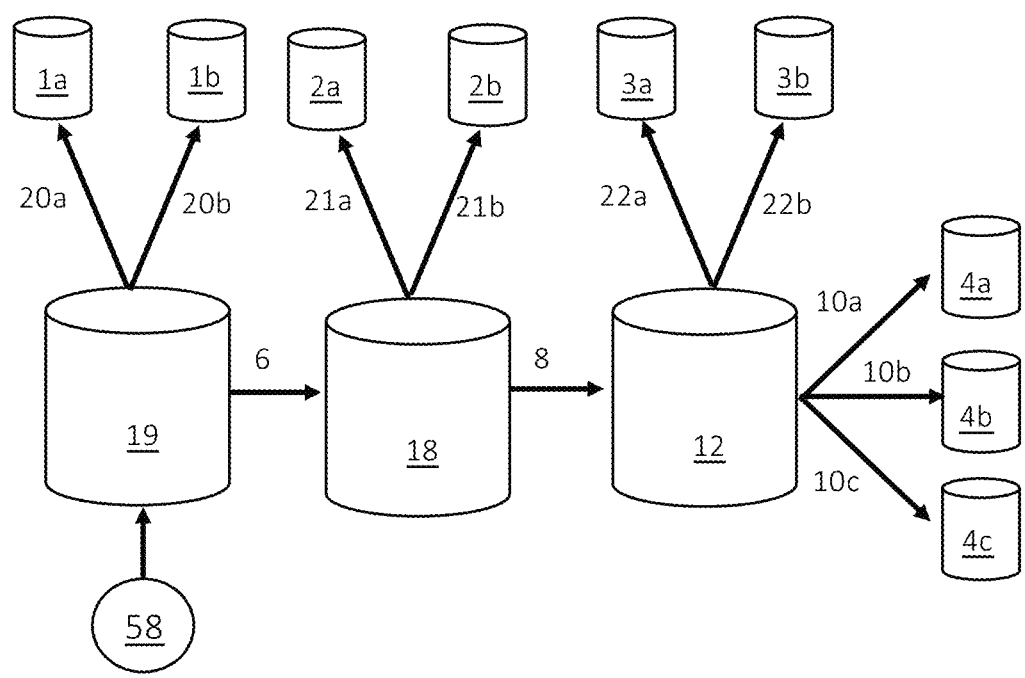
FIG. 8 illustrates a diagram of an example reactor according to principles described herein.

Also, various contents from environments may be purified for a separate process. Turning to FIG. 8, examples are provided that show contents taken from an environment and purified for a separate process. Contents 20a and 20b from the mixing tank 19 are purified for respective processes 1a and 1b. Contents 21a and 21b from the ASB tank 18 are purified for respective processes 2a and 2b. Contents 22a and 22b from the AD tank 12 are purified for respective processes 3a and 3b. Contents 10a, 10b, and 10c are purified for respective processes 4a, 4b, and 4c. In an example, at least a portion of the ASB treated biomass from the ASB tank 18 is purified and concentrated for at least one other process outside of the AD tank 18. The portion of the ASB treated biomass 21a, 21b may be separated, or separated and purified, to be used for a process outside of the AD tank 12. For example, at least a portion of the unsolubilized components may be reintroduced into the ASB tank 18 for future ASB digestion.

In an example, at least a portion of the ASB treated biomass serves as a feedstock or reagent for crude oil or fuel production or as at least one precursor for at least one synthetic process or other process. In another example, biogas methane is the portion of AD biogas that is separated and used as one or more precursors for at least one synthetic process or other process. Examples of synthetic processes include oxygenated aromatic compounds for synthesis of medicines and new materials.

Purification may occur before separation as well. In an example, at least a portion of the AD biogas from the AD tank 12 is purified in a respective processing treatment (not shown) before being separated into different contents 22a and 22b or before being used to produce a pure biogas.

In another example, contents recycled as shown in FIG. 7 are purified. For example, contents from the AD tank 12 may go through a purification processing treatment (not shown) before being received within the ASB tank 18.

In an example, the AD tank 12 may provide at least one nutrient to the ASB tank 18 before the ASB tank 18 treats the biomass. In another example, the AD satellite tank 14 provides at least one nutrient to the ASB tank 18 before the ASB tank 18 treats the biomass 6. In another example, the AD tank 12 mixes and heats biomass with water and provides $CO_2$ and nutrients from the AD tank 12 to the ASB tank 18 before the ASB tank 18 treats the biomass. The contents being provided may or may not have been recycled by the environment providing them.

In one example, bicarbonate or another base from the AD tank 12 is recycled to the ASB tank 18 to maintain growth conditions. In another example, at least a portion of $CO_2$ and nutrients are removed from the AD tank 12 and recycled to at least one of the mixing tank 19 and the ASB tank 18 to displace oxygen or air.

Figure 18:
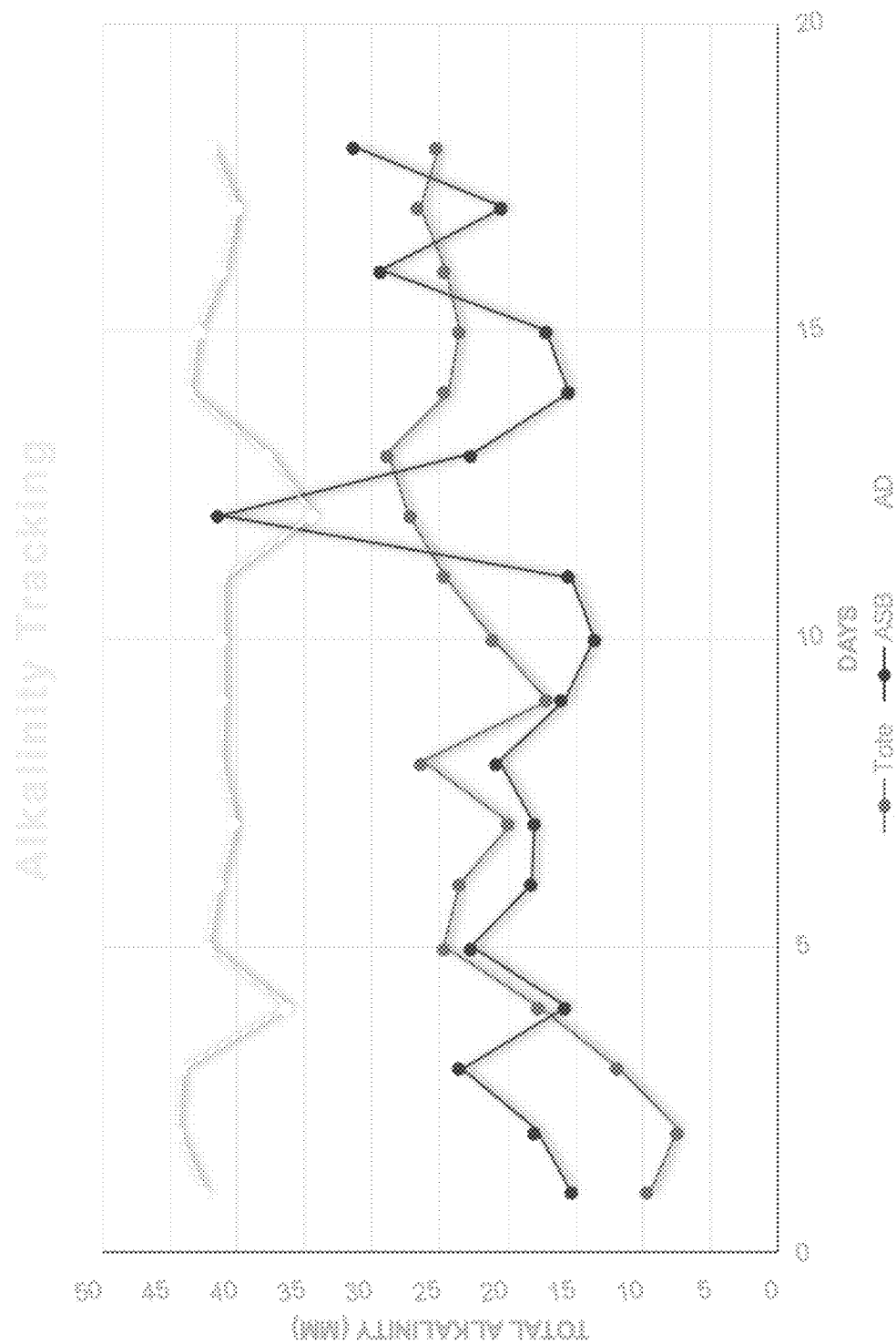
FIG. 18 illustrates a graph that shows alkalinity within the ASB tank achieved by recycling bicarbonate from the AD tank.

FIG. 18 includes a graph that shows the alkalinity achieved by recycling bicarbonate from the AD tank 12. Tests show that alkalinity from AD effluent can be used to raise the alkalinity of the ASB tank 18.

In another example, oxygen is removed from at least one of the AD tank 12 and ASB tank 18 and any input streams with or without recycling. In an example, $CO_2$ and bicarbonate produced in the AD environment are recycled to the ASB environment to mitigate pH changes and reduce oxygen concentration in the ASB environment. Oxygen removal can be accomplished by flushing the AD 12 and ASB tanks 18 with $CO_2$ from combustion or gas processing or by other removal means. Note that contents being recycled or released may be in a gas phase, liquid phase, dissolved in a solution, or in another form.

During ASB treatment in the ASB tank 18, the pH level naturally drops and becomes acidic. Bicarbonate ions that are formed in the AD tank 12 may be removed from the AD tank 12 and put back into the ASB tank 18, which neutralizes the pH level of the ASB tank 12. In this manner, matter in the AD tank 18 is recycled in the ASB tank 12. This act may make it unnecessary to buy a base to neutralize the pH level in the ASB tank 12, and is thus a cost-saving step. In another example, an ammonia scrubber (not shown) is included in the system to scrub contents that are recycled from the AD tank 12. The scrubber strips out ammonia and keeps the concentration below a toxic level.

Example Reactor Systems

The description and examples below are provided, followed by reference to FIGS. 9-14 in relation to principles discussed herein.

An example reactor for conversion of biomass into biogas comprises an ASB treatment tank containing anaerobic organisms and an AD tank that receives ASB tank effluent. The ASB tank receives biomass effluent that includes nonsolubilized lignocellulosic components and treats the biomass effluent under conditions such that the anaerobic organisms reproduce and solubilize the lignocellosic components. Upon receiving the ASB tank effluent, the AD tank contains anaerobic bacteria that convert organism metabolic products of the lignocellulosic components into biogas under anaerobic digestion conditions. Outputs from the AD tank including the biogas and a slurry of undigested biomass.

An example reactor may further comprise a mixing tank where the biomass is mixed with water, heated, and components in the biomass are solubilized. The effluent of biomass suspended in water from the mixing tank is then transferred to the ASB tank.

An example reactor may further comprise at least one satellite reservoir that provides at least one of a bacteria, nutrient, and other content discussed herein, to at least one of the ASB tank and AD tank according to principles discussed herein.

An example reactor further comprises an AD tank that contains anaerobic bacteria and that receives contents comprising solubilized biomass. The anaerobic bacteria is to convert organism metabolic products of lignocellulosic components of the solubilized biomass into biogas under anaerobic digestion conditions. Outputs from the AD tank include the biogas and a slurry of undigested biomass. An AD satellite reservoir is used to supply one or more microbial species to the AD tank to support conversion of the organism metabolic products.

An example method of converting biomass into biogas includes 1) treating biomass in an ASB environment with anaerobic organisms that solubilize and metabolize lignocellulosic components of the biomass and then 2) treating the treated biomass in an AD environment with archaea and anaerobic bacteria that convert products of the lignocellulosic components in the treated biomass into biogas under anaerobic digestive conditions.

Another example method of converting biomass into biogas includes that biomass received by the ASB environment is 1) at least partially solubilized by at least one of chemical or mechanical treatment prior to the biomass being introduced into the ASB environment. Further examples include that the biomass is solubilized by at least one of chemical or mechanical treatment in the mixing tank prior to the biomass being introduced into the ASB tank.

An example method may further comprise providing conditions to produce bicarbonate in the AD environment. The bicarbonate may be recycled to the ASB environment.

An example method further comprises mixing and heating the biomass with water before treating the biomass in the ASB environment.

An example method further comprises recovering heat from one of more of the AD environment and the ASB environment.

An example method further comprises buffering the ASB environment to produce acetate and lactate as part of the solubilized components. The ASB environment may further be operated to produce predominantly acetate, with little or no carbon dioxide.

An example method further comprises favoring ASB acetate ion production over lactate ion production within the ASB environment to produce a reduced $CO_2$ stream in the AD environment.

Large scale production of converting biomass into biogas is anticipated based on examples and principles discussed herein.

Alternatives include no power generation, such that the motors are replaced by, or used in conjunction with, electrical generators.

In an example, $CO_2$ and bicarbonate that are produced in the AD tank are recycled back to the ASB tank.

At least a portion of the biogas may be biogas methane that is burned by an AD electrical generator. In this manner, the AD tank provides its own power to the system.

Figure 9:
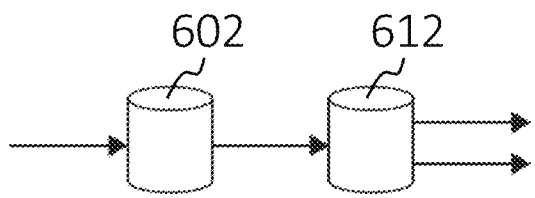
FIG. 9 illustrates a diagram of an example reactor according to principles described herein.

Turning to FIG. 9, a reactor is shown that includes an ASB tank 602 and an AD tank 612.

Figure 10:
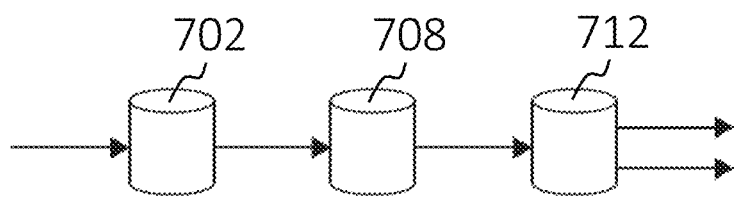
FIG. 10 illustrates a diagram of an example reactor according to principles described herein.

Turning to FIG. 10, a reactor is shown that includes a mixing tank 702, an ASB tank 708, and an AD tank 712.

Figure 11:
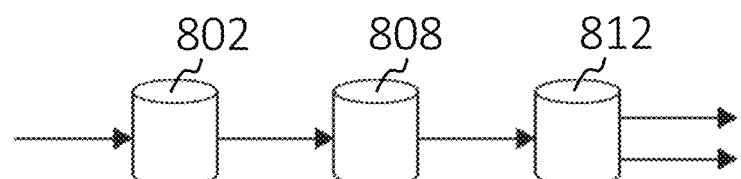
FIG. 11 illustrates a diagram of an example reactor according to principles described herein.

Turning to FIG. 11, a reactor is shown that includes a mixing tank 802 that mixes and heats, an ASB tank 808, and an AD tank 812.

Figure 12:
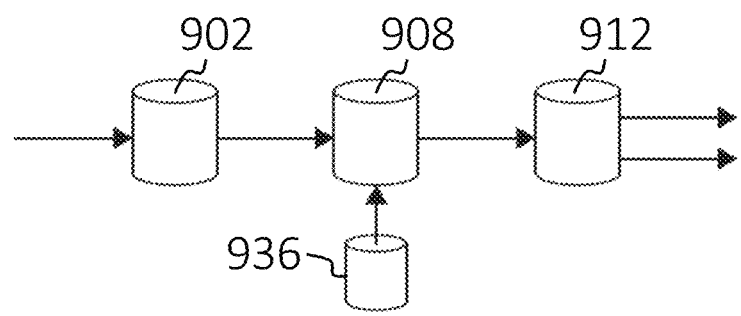
FIG. 12 illustrates a diagram of an example reactor according to principles described herein.

Turning to FIG. 12, a reactor is shown that includes a mixing tank 902, an ASB tank 908 that includes an ASB satellite reservoir 936, and an AD tank 912.

Figure 13:
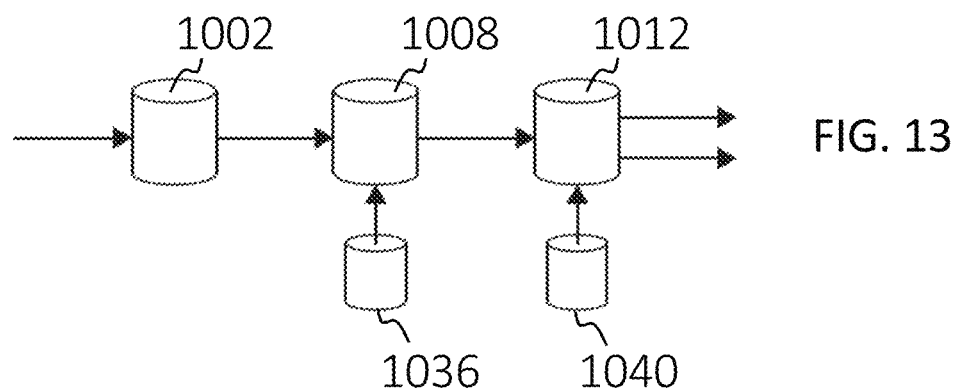
FIG. 13 illustrates a diagram of an example reactor according to principles described herein.

Turning to FIG. 13, a reactor is shown that includes a mixing tank 1002, an ASB tank 1008 that includes an ASB satellite reservoir 1036, and an AD tank 1012 with an AD satellite reservoir 1040.

Figure 14:
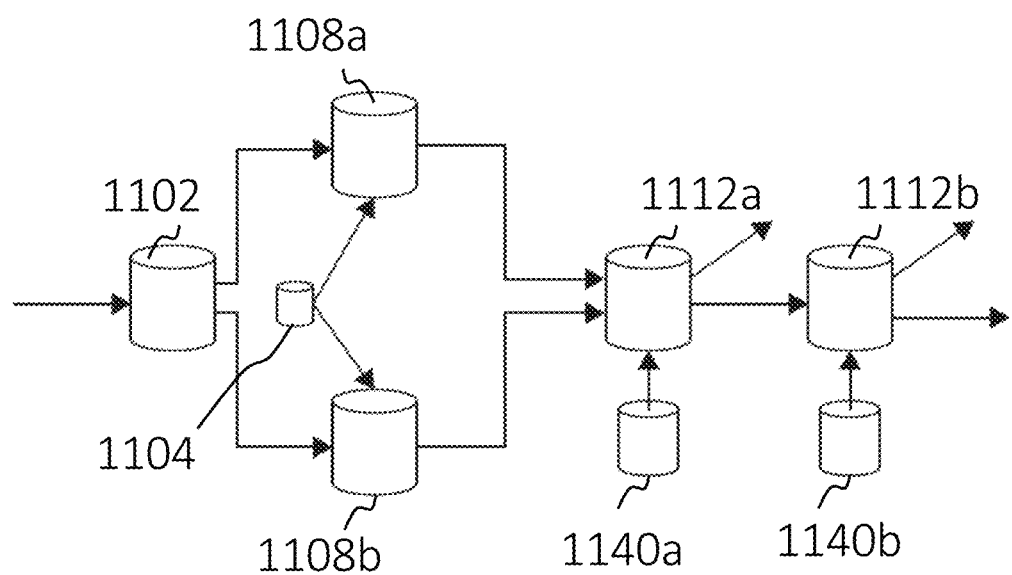
FIG. 14 illustrates a diagram of an example reactor according to principles described herein.
Figure 15A:
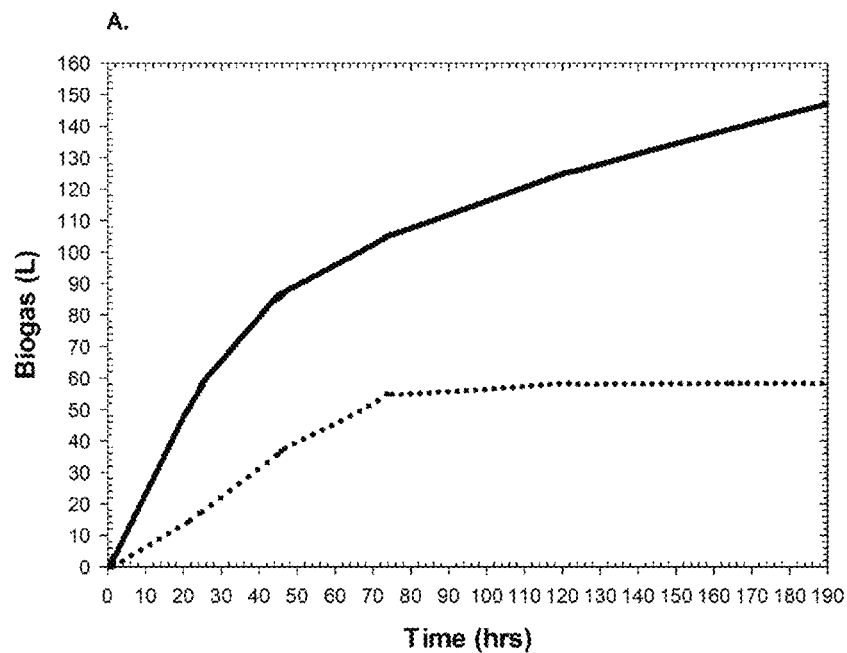
FIGS. 15A and 15B illustrate graphs showing exemplary biogas volume and biogas rate of production v. time.
Figure 15B:
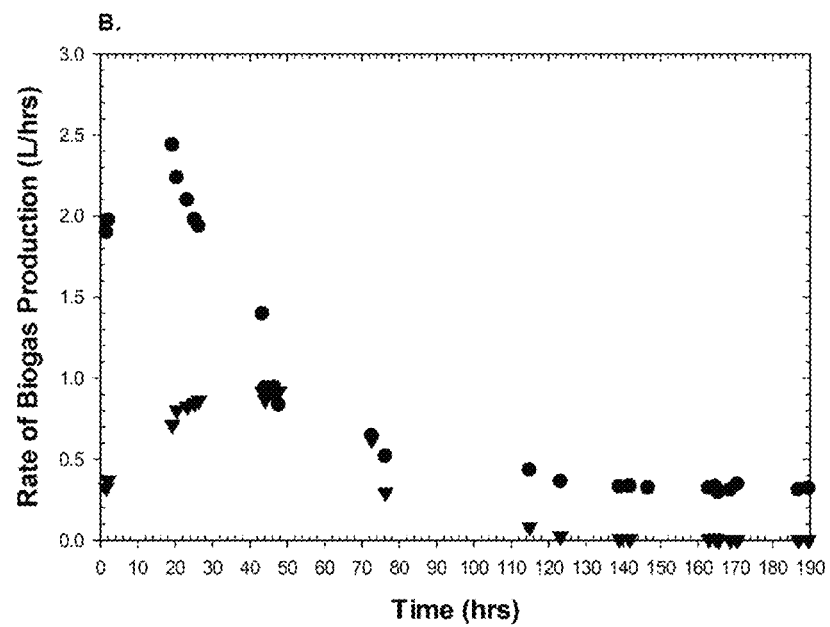
Figure 16A:
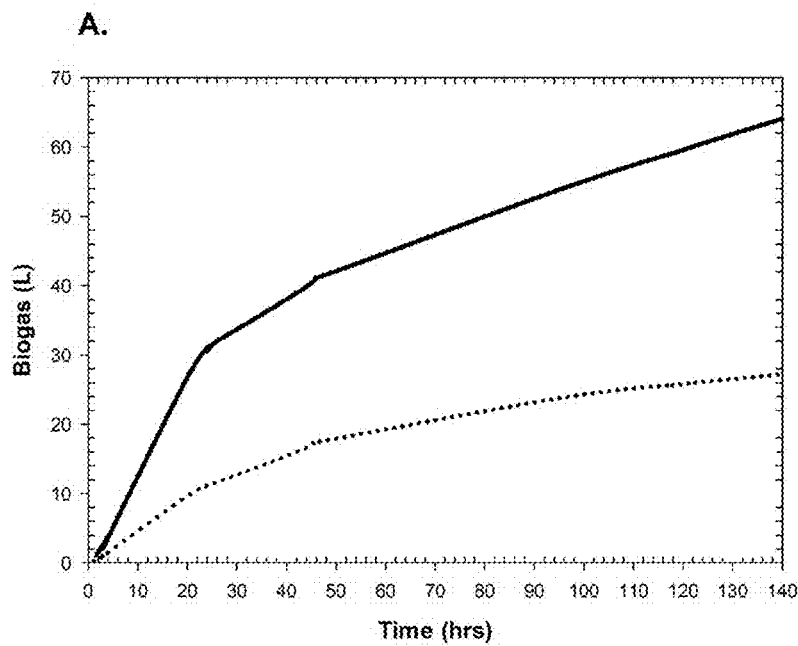
FIGS. 16A and 16B illustrate graphs showing exemplary biogas volume and biogas rate of production v. time.
Figure 16B:
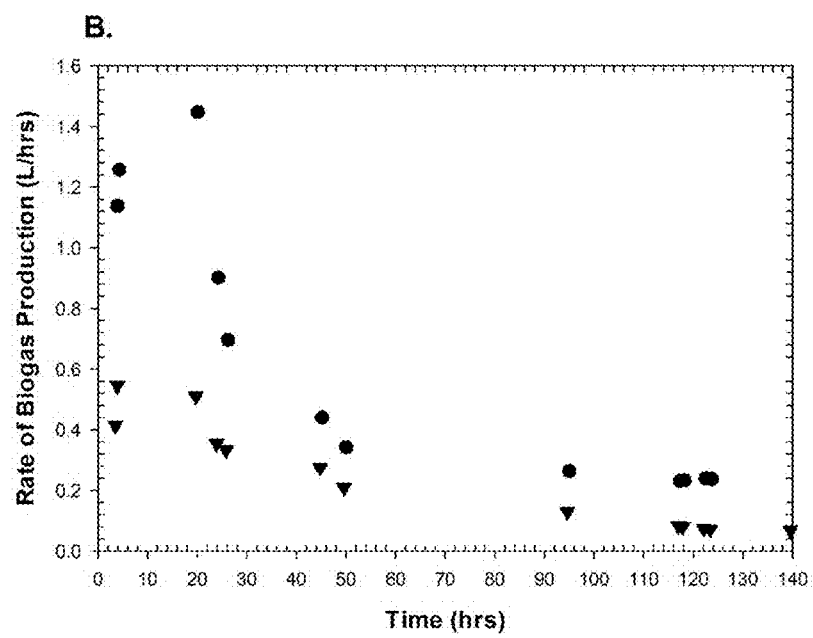
Figure 17:
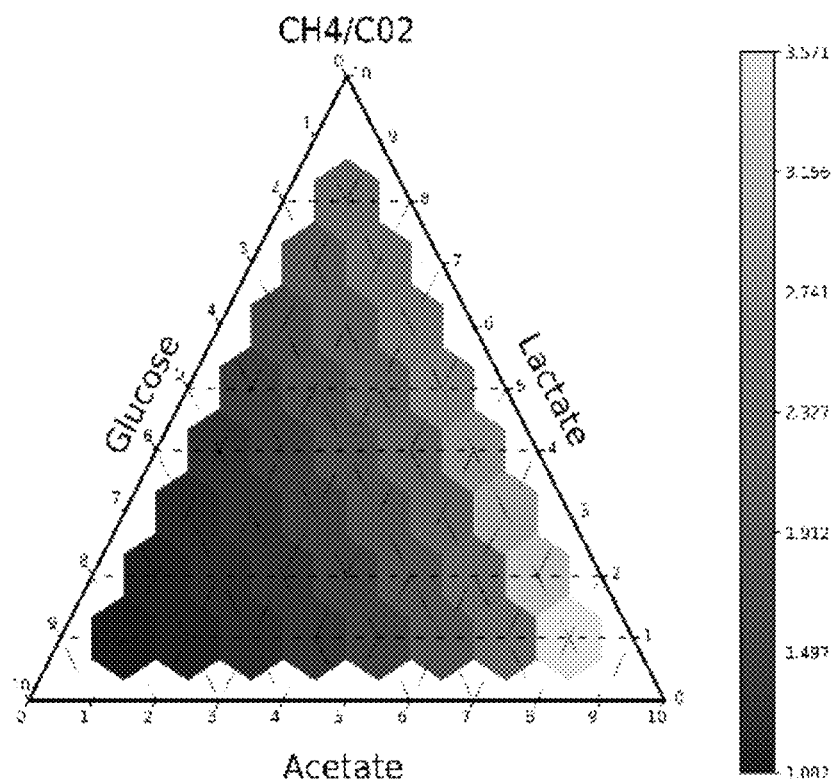
FIG. 17 illustrates the methane content of the biogas produced by differing mixtures of acetate, lactate and glucose.

Turning to FIG. 14, a reactor is shown that includes a mixing tank 1102, two ASB tanks 1108a and 1108b, an ASB satellite reservoir 1104 that provides one or more of bacteria, trace nutrients, or other matter to the two ASB tanks 1108a and 1108b, and two AD tanks 1112a and 1112b, each AD tank having its own respective AD satellite reservoir 1140a and 1140b.

Other reactors are anticipated that incorporate principles discussed herein.

Section A
Example Kinetic Model

A possible model describes ASB treatment with acetate as the major ASB treatment product.

The ASB Tank in this Model Includes the Following Example Reactions:

Cellulose(s)+$H_2O$(l)→glucose(aq) and glucose(aq)+ 3$OH^-$(aq)→3$CH_3COO^-$(aq)+3$H_2$(l)

$d[CH_3COO^-]/dt=-\Delta Gc=-(\Delta G°+RT \ln([CH_3COO^-]^3/[OH^-]^3[glucose])[CB]$ $d[glucose]/dt=k_4$[active enzyme][substrate sites]−(⅓) $d[CH_3COO^-]/dt$ $d[CB]/dt=k_5[CB]→d[CB]/[CB]=k_5t→\ln([CB]/[CB]_0)= k_5(t-t_0)→[CB]_t=[CB]_0 e^{k_5(t-t_0)}$ $d$[substrate sites]$/dt=a[(TSS)_0-(d(TSS)_t/dt)]$ $d$[active enzyme]$/dt=d[CB]/dt=(n_{CB0}e^{k_7t})/V_{ASB}$ An example kinetic model for an ASB treated substrate may be used for the ASB effluent that enters the AD tank.

The AD Tank in this Model Includes the Following Example Reactions:

$CH_3COO^-$(aq)→$CH_4$(g)+$HCO_3^-$(aq)

and VS→$CH_4$(g)+$CO_2$(g)

$d[CH_3COO^-]V_f/dt=-d(P_{CH4}V_g/RT)/dt=\Delta_8 Gc= (\Delta_8 G°+RT \ln(P_{CH4}[HCO_3^-]/[CH_3COO^-]))$[acetoclastic methanogens]

$d[CH_3COO^-]/dt=-k_8[CH_3COO^-]$[acetoclastic methanogens]

$d[VS]=-k_9[VS]$[oxidative methanogens]$=d (2bP_{CO2}V_g/V_lRT)/dt$

Symbols
s, l, aq=solid, liquid, gas phase
[ ]=concentration of substance
$\Delta_n G$=Gibbs energy change for reaction n
$\Delta_n G°$=standard Gibbs energy change for reaction n
c=conductance
R=gas constant
T=absolute (Kelvin) temperature
CB=*C. bescii*
$k_n$=rate constant for reaction n
t=time
$n_{CB0}$=number of *C. bescii* cells at time=0
$V_{ASB}$=volume of ASB tank
$V_l$=liquid volume in AD tank
$V_g$=volume of biogas produced to time t
$P_x$=pressure of x
VS=volatile solids input to AD
TSS=total suspended solids input to ASB
a=cellulose sites per TSS
b=accessible sites per VS Some possible results are anticipated as follows—
1. The *C. bescii* inoculum does not survive or grow as it should. In that case, the treated and control AD tank results should be very close to the same.
2. If glucose is produced from cellulose much faster than *C. bescii* can digest it, then ASB effluent in the AD tank produces gas at a higher rate than the control but the methane content is not as high as it should be.
3. If the ASB tank is fed at too high a concentration of substrate, the *C. bescii* grows to a stationary phase and stops making enzymes before ASB treatment is complete. In this case, the biogas from the treated material is greater and produced faster and has a higher methane content, but does not get good carbon conversion to biogas.

The ASB treatment tanks in the model may be filled according to
$V_t = V_0 e^{kt}$
$V_t$=volume at time t
$V_0$=volume at time zero with *C. bescii* seed
t=time in hours
k=constant depending on doubling time of *C. bescii* on a particular substrate
Table B shows exemplary k value corresponding to doubling time.

TABLE B

| doubling time/hours | k/hours$^{-1}$ |
|---|---|
| 2 | 0.346574 |
| 2.5 | 0.277259 |
| 3 | 0.231049 |
| 3.5 | 0.198042 |
| 4 | 0.173287 |
| 4.5 | 0.154033 |
| 5 | 0.138629 |

Implementing the model above should maintain an exponentially growing culture and maximize output of exozymes.

To further design the treatment, the following formulas may be helpful—
Gas composition from stoichiometry of carbon going into AD tank.

$C_{in} = 2xCH_3COO^- + 3yCH_3CH(OH)COO^- + 6zC_6H_{12}O_6$
(products of ASB treatment)

$C_{out} = aCH_4 + bCO_2 + cHCO_3^-$ (products of methanogenesis)

x, y, z, a, b, and c are in units of moles of compound.
From the reactions of methanogenesis $xCH_3COO^- + xH_2O = xCH_4 + xHCO_3^- \ yCH_3CH(OH)$
$COO^- + yH_2O = yHCO_3^- + 1.5yCH_4 + 0.5yCO_2$ $zC_6H_{12}O_6 = 3ZCH_4 + 3ZCO_2$ $a = x + 1.5y + 3z$ $b = 0.5y + z$ $c = x + y$ If x, y and z (acetate, lactate, and glucose) are measured and total C in the filtered solution come from ASB treatment, gas composition and bicarbonate production can be predicted.

Discussion of Chemistry and Thermodynamics
This is a discussion of chemistry and thermodynamics of anaerobic and thermophilic pre-digestion with *C. bescii* followed by anaerobic digestion to produce biogas from organic wastes as a renewable energy source.

ASB Digestion with *C. bescii*.
An example of the present process according to principles discussed herein takes place in three consecutive tanks:
1. An organic waste containing polymeric materials suspended in water is first added to a mixing tank at 75° C. where some hydrolysis occurs. $O_2$ is removed by a reaction with organic material, and the suspension is pasteurized.
2. Digestion with *C. bescii* takes place in an ASB tank at 75° C. The pre-digestion reactions in the ASB tank includes:
Hydrolysis of polymeric material catalyzed by exozymes produced by *C. bescii*

Lignin+$H_2O$→oligomers of substituted phenolics

Cellulose+$H_2O$→glucose,C($H_2O$)

Polyhydroxyalkanoates+$H_2O$→hydroxyalkanoates

These hydrolysis reactions are all exergonic, i.e. the Gibbs energy change is negative and relatively rapid at 75° C. The rate of reaction is proportionate to the concentration of enzyme and number of sites for attack on the polymeric substrate.

$d[\text{products}]/dt = k_{cat}[\text{exozymes}][\text{polymer surface area}]$

For the reaction to proceed, conditions must be such that $\Delta G$ is negative. $\Delta H° \approx 0$ and $\Delta S°$ is also small, so $\Delta G°$ is also small, particularly at low temperature. Therefore, to obtain a significantly negative $\Delta G$ requires removal of products to keep [products] small and an elevated temperature to obtain a significant rate. Use of a hyperthermophile is required to obtain commercially viable rates. (Fungi that do this at low temperature are all extremely slow growing.) Products are removed by metabolism by *C. bescii* and by dilution by incoming material from the mixing-hydrolysis tank.

Some of the products of hydrolysis are then metabolized by *C. bescii* as follows—

C($H_2O$)→acetic acid,$CH_3COOH$ and lactic acid, $CH_3CH(OH)COOH$ $CH_3COOH + HCO_3^- \rightarrow CH_3COO^- + H_2O + CO_2(g)$ $CH_3CH(OH)COOH + HCO_3^- \rightarrow CH_3CH(OH)COO^- + H_2O + CO_2(g)$ Other saccharides are metabolized similarly to glucose. Hydroxyalkanoates are also metabolized by *C. bescii*, but the products are unknown. All of these reactions are intracellular. The first reaction is a disproportionation reaction and has near zero Gibbs energy change. The second and third reactions are acid-base reactions that produce gas and have a significant negative Gibbs energy change that powers the growth and activities of *C. bescii*. $\Delta G°=-9$ kJ/mole, $\Delta H°$ is $-9$ kJ/mole, and $\Delta S°$ is $\approx 0$ for the reaction to produce $CO_2$(aq). The entropy of $CO_2$(g) is 158 J/K mole, so $\Delta G°\approx -56$ kJ/mole at 25° C. for the reactions as written. $\Delta G°$ at 80° C. is $\approx -65$ kJ/mole.

$\Delta G°$ values (kJ/mole) for reaction of various bases with acetic and lactic acid are given in Table D.

TABLE D $\Delta G°$ values (kJ/mole) for reaction of various bases with acetic and lactic acid are given in the Table.

| acid | base | | | |
|---|---|---|---|---|
| | $HCO_3^-$(aq) | $OH^-$(aq) | $NH_3$(aq) | $CaCO_3$(s) |
| acetic | −17.5 | −52.8 | −25.8 | +17.1 |
| lactic | −22 | −58 | −31 | +12 |

Because these reactions in the sequence are the only reactions with relatively large negative $\Delta G$ values, production of $CO_2$ gas, water, and other products from reaction of the acids produced with a base is essential for growth of *C. bescii*. Note that $-\Delta G$ gets numerically smaller as the concentration of acid anion increases, so the reaction may slow as these concentrations increase and there may be a practical limit for bases other than bicarbonate. $\Delta G$ is sufficiently large and negative for bicarbonate ion that this limit will not be reached in realistic systems buffered with this base.

These processes are related to the growth rate of *C. bescii* which is also relatively fast with doubling times of 2 to 5 days depending on the substrate (See Table A1 above).

3. The products of the reactions in the ASB tank are transferred to the anaerobic digestion (AD) tank where the reactions may be as follows—

$$CH_3COO^- + H_2O \rightarrow CH_4(g) + HCO_3^- (100\% \text{ CH}_4)$$

$$2CH_3CH(OH)COO^- + 2H_2O \rightarrow 3CH_4(g) + 2HCO_3^- + CO_2(g) (75\% \text{ CH}_4)$$

$$2C(H_2O) \rightarrow CH_4(g) + CO_2(g) (50\% \text{ CH}_4)$$

The methane may thus be increased. The methane content of the biogas produced from anaerobic digestion of each of these substrates is given in parentheses. When catalyzed by acetoclastic methanogens, these reactions are relatively fast with half times of 2 to 5 days depending on the concentrations of substrates. The oligomers of substituted phenolics are probably not metabolized by acetoclastic methanogens, but are partially metabolized by oxidative methanogenesis to produce biogas with about 60% methane. The chart in FIG. 14 shows the methane content of the biogas produced by differing mixtures of acetate, lactate, and glucose.

The bicarbonate produced in these reactions maintains the pH in the AD tank at slightly basic levels, so no further pH control is necessary. Note that bicarbonate ion is not volatile and will not contribute a significant amount of $CO_2$ to the biogas as long as the AD pH is above neutral. The amount of bicarbonate produced by AD is the same as the amount of bicarbonate consumed by the reactions in the ASB tank. Therefore, bicarbonate from the AD can be recycled to supply most or all of the bicarbonate needed in the ASB reactions.

Process Variables
Mixing/Hydrolysis Tank Process Variables
1. $O_2$ concentration in the feedstock.
2. Feedstock composition, e.g., waste activated sludge (WAS) or manure
ASB Tank Process Variables
1. % solids in suspension fed to ASB
2. temperature
3. pH
4. Bacteria (e.g., *C. bescii*) concentration and phase, i.e. exponential growth or stationary
5. Recycle or base addition rate
6. Stirring rate
7. Retention time in ASB
8. Alkalinity
9. Redox potential Note that there are at least two processes in the ASB Tank, namely, hydrolysis of the feedstock and metabolism of the products of hydrolysis. The rates of these two processes have differing dependencies on variables 1 through 5. The composition of the effluent that is fed to the AD tank thus has a multivariate dependence on all of the above variables. The composition of the effluent from ASB tank determines the composition of the biogas produced by anaerobic digestion and the optimum conditions for anaerobic digestion operation.

AD Tank Process Variables
1. Composition of ASB effluent
2. Retention time
3. Temperature
4. pH
5. Bacteria and Archaea concentration and phase (e.g., relative and absolute concentrations)
6. Stirring
7. Alkalinity
8. Redox potential
Other Variables that Affect the Process
1. Sulfur chemistry
2. Nitrogen chemistry
3. Micronutrients
4. Augmentation of AD with acetoclastic methanogens
5. Growth rates of ASB bacteria (e.g., *C. bescii*) on different substrates Governing Equations for Engineering the System. //Fix Below
Governing Equations for ASB
Measurement as f(Time)
Rate of growth of ASB bacteria (e.g., *C. bescii*, etc.)

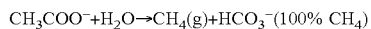

of live *C. bescii*/L

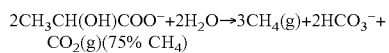

COD of Supernatant, OAc—, Lac-

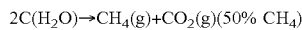

VSS, enzyme activity, COD

Variable Definitions

[n]=concentration of ASB bacteria (e.g., *C. bescii*), number/liter
[Sm]=concentration of substrates for metabolism, Cmol/liter
[Pm]=concentration of products of metabolism, Cmol/liter

[Sh]=concentration of substrates for hydrolysis, Cmol/liter
[E]=concentration of active enzyme, enzyme activity units/liter
[Ph]=concentration of products of hydrolysis, Cmol/liter
(dVf/dt)=flow rate of feedstock, liters/hour
VASB=volume of ASB tank, liters
[Sin]=concentration of volatile solids in feedstock, Cmol/liter
The ks are all rate constants with units determined by variables in the equation.

Conclusions

Solution to these differential equations will depend on feedstock, but in general there are two maxima, one that maximizes [Pm] and one that maximizes [Ph]. Short ASB retention times (around 12-20 hours) maximizes [Pm] and longer ASB retention times (around 48+ hours) maximizes [Ph]. The output from AD depends on which you maximize. Maximizing [Pm] maximizes the methane content in biogas and maximizing [Ph] maximizes total biogas and waste destruction.

These equations are based on an assumption that all of the volatile solids can be hydrolyzed and solubilized. That can easily be fixed if necessary by adding a constant multiplier on Sh.

Governing Equations for AD.

The output from the ASB is the input to AD, which has two components:

Products of *C. bescii* metabolism, i.e. acetate and lactate, at concentration [Pm].

Products of hydrolysis from enzymatic action, i.e. saccharides, polyphenols, hydroxyalkanoates, etc. with a total concentration of [Ph].

$[Ph]=[acetate]+[lactate]+[saccharides]+[hydroxyalcanoates]+[polyphenols]$ in Cmol/liter $d\text{CH}_4/dt=-0.5d[acetate]/dt-0.5d[lactate]/dt-0.5d[saccharides]/dt-xd[hydroxyalcanoates]/dt-yd[polyphenols]/dt$ $x=\text{CH}_4/\text{Cmol hydroxyalkanoate}$, $y=\text{CH}_4/\text{Cmol polyphenol}$ $d[\text{CO}_2]/dt=-0.16d[lactate]/dt-0.5d[saccharides]/dt-ad[hydroxyalcanoates]/dt-bd[polyphenols]/dt$ $a=\text{CO}_2/\text{Cmol hydroxyalkanoate}$, $y=\text{CO2}/\text{Cmol polyphenol}$ $d[\text{HCO}_3^-]/dt=-0.5d[acetate]/dt-0.33d[lactate]/dt-cd[hydroxyalcanoates]/dt$ $c=\text{HCO}_3^-/\text{Cmol hydroxyalkanoate}$ Conclusions These equations are based on an assumption that all volatile solids are digested.

Recycle to recover bicarbonate has not been included, but could be by adding more terms to the equations.

Engineering Tank Volumes

Relative tank sizes determine retention time in a continuous flow system

VH=(dV/dt)*10 hours
VASB=(dV/dt)*(doubling time)
VAD=(dV/dt)*(t %) (t %) is the time required to obtain a set percentage of potential biogas production.
VH/VASB/VAD=1/0.82/7.2 to 1/0.82/14 for manure
VH/VASB/VAD=1/0.7/8.3 to 1/0.7/11.2 for WAS The invention has been described with reference to various specific and preferred embodiments and techniques. Nevertheless, it is understood that many variations and modifications may be made while remaining within the spirit and scope of the invention.

What is claimed is:

1. A method for biogas production by a system comprising an anaerobic secretome bioreactor environment that comprises a synthetic microbial community consisting of at least one type of microorganism selected from extremophile thermophilic anaerobic microorganisms that are essentially acidogens and acetogens capable of producing a secretome of exozymes, comprising:
    predigesting lignocellulose comprised in biomass by treating the biomass with the secretome of exozymes in the anaerobic secretome bioreactor environment through hydrolysis, acidogenesis, and acetogenesis to solubilize and metabolize a substantial portion of the lignocellulose, the treating performed at a thermophilic temperature of 70 to 85 degrees Celsius so as to support growth of the at least one type of microorganism under essentially acidogenic, acetogenic, and non-methanogenic conditions, where the treating includes pasteurizing the synthetic microbial community such that it becomes essentially free of non-thermophilic microorganisms;
    digesting, in an anaerobic digestion reactor environment of the system, the treated biomass, where the digesting includes maintaining a temperature that supports growth in the anaerobic digestion reactor environment of non-thermophilic anaerobic microbes that include anaerobic bacteria and archaea and that are capable of digesting the treated biomass through methanogenesis so as to produce methane; and
    recycling heat or at least a portion of the treated biomass between the anaerobic secretome bioreactor environment and the anaerobic digestion reactor environment.

2. The method of claim 1, further comprising providing, to the anaerobic secretome bioreactor reactor environment, thermophilic anaerobic microorganisms that include bacteria that comprise at least one type of bacterium of genus *Caldicellulosiruptor*, *Clostridium*, *Thermoanaerobacterium*, or other bacteria with comparable or otherwise suitable properties for predigesting the lignocellulose.

3. The method of claim 1, further comprising:
    cooling the treated biomass prior to the digesting in the anaerobic digestion reactor environment; or
    heating effluent from the anaerobic digestion reactor environment prior to the recycling the effluent into the anaerobic secretome bioreactor environment.

4. The method of claim 1, further comprising separating at least a portion of the treated biomass that comprises unsolubilized lignocellulose to be used for another process including recycling the portion back into the anaerobic secretome bioreactor environment for further predigesting.

5. The method of claim 1, further comprising maintaining a supply of at least one type of nutrient or at least one type of the non-thermophilic anaerobic microbes suitable for supporting the production of the biogas from the treated biomass.

6. The method of claim 5, further comprising supplying to the anaerobic digestion reactor environment at least a portion of the supply from an anaerobic digestion satellite reservoir.

7. The method of claim 5 where the supply is grown on a substrate that is the same as or substantially similar to the biomass in the anaerobic digestion reactor environment.

8. The method of claim 1, further comprising maintaining and providing at least one type of bacteria, nutrient, pH adjusting chemical, or other matter to the anaerobic secretome bioreactor environment as desired or needed for at least one of the following:
1) maintaining the synthetic microbial community as suited for the anaerobic secretome bioreactor environment;
2) alleviating the need for trace elements to be added to the anaerobic secretome bioreactor environment, depending on chemical characteristics of the biomass;
3) conditioning *C. bescii* to digest the biomass in the anaerobic secretome bioreactor environment, where the *C. bescii* is included in the at least one type of microorganism selected from the extremophile thermophilic anaerobic microorganisms;
4) speeding up the predigesting in the anaerobic secretome bioreactor environment by avoiding time that otherwise would be required for *C. bescii* to grow in the anaerobic secretome bioreactor environment;
5) adding bicarbonate or another base to the anaerobic secretome bioreactor environment so as to maintain pH and support metabolism of the lignocellulose; and
6) promoting the predigesting of the lignocellulose.

9. The method of claim 1, further comprising mixing the biomass with water prior to predigesting the lignocellulose so as to mitigate pH changes and promote hydrolysis of the lignocellulose.

10. The method of claim 1, further comprising removing, via a biogas conditioner, $CO_2$ from the biogas and recycling the $CO_2$ to at least one of a mixing tank, the anaerobic secretome bioreactor environment, and the anaerobic digestion reactor environment so as to displace oxygen or air in the foregoing at least one.

11. The method of claim 1, further comprising recycling heat from combustion of the biogas to the anaerobic secretome bioreactor environment.

12. The method of claim 1, further comprising;
recycling carbon dioxide or bicarbonate from the anaerobic digestion reactor environment to the anaerobic secretome bioreactor environment; and
controlling the recycling to or pH in the anaerobic secretome bioreactor environment so as to displace oxygen or air within the anaerobic secretome bioreactor environment.

13. The method of claim 1, further comprising:
mixing water or other suitable liquid with solid effluent from the anaerobic secretome bioreactor environment or from the anaerobic digestion reactor environment, where the solid effluent comprises at least a portion of the lignocellulose, where the portion was not completely solubilized during the predigesting, the mixing resulting in a slurry in which the not-completely-solubilized lignocellulose is suspended; and
recycling the slurry into the anaerobic secretome bioreactor environment for further predigesting of the not-completely-solubilized lignocellulose.

14. The method of claim 1, further comprising supplying contents from at least one of an anaerobic secretome bioreactor satellite reservoir and an anaerobic digestion satellite reservoir to the respective anaerobic secretome bioreactor environment and the anaerobic digestion reactor environment, the contents including at least one type of bacteria, nutrient, pH adjusting chemical, or other matter, where the content is maintained in conditions substantially similar to that of the respective anaerobic secretome bioreactor environment or the anaerobic digestion reactor environment to which they are supplied.

15. A method for biogas production, comprising:
pretreating biomass comprising lignocellulose in an anaerobic secretome bioreactor environment that comprises a synthetic microbial community consisting of at least one type of microbe selected from thermophilic anaerobic microorganisms that consist essentially of non-methanogenic acidogens and acetogens, wherein the at least one type of microbe produces a secretome of exozymes that solugilize and metabolize a substantial portion of the lignocellulose through hydrolysis, acidoqenesis, and acetoqenesis, where the pretreating includes supporting growth of the at least one type of microbe in the anaerobic secretome bioreactor environment via a thermophilic temperature and a substantially neutral pH, and under essentially acidogenic, acetogenic, and non-methanogenic conditions so as to pasteurize the biomass such that it becomes essentially free of non-thermophilic microbes;
treating the pretreated biomass in an anaerobic digestion reactor environment, where the treating includes supporting growth of non-thermophilic anaerobic microbes that include anaerobic bacteria and archaea and that are capable of digesting the pretreated biomass through methanogenesis so as to produce methane.

16. The method of claim 15, further comprising:
supplying contents from an anaerobic secretome bioreactor satellite reservoir to the anaerobic secretome bioreactor environment; or
supplying contents from an anaerobic digestion satellite reservoir to the anaerobic digestion reactor environment.

17. The method of claim 15, further comprising controlling an oxygen level, a temperature range, a pH, or an alkalinity within the anaerobic secretome bioreactor environment so as to maintain substantially optimal growth of the least one type of microbe.

18. The method of claim 15, further comprising recycling bicarbonate produced in the anaerobic digestion reactor environment to the anaerobic secretome bioreactor environment so as to control alkalinity within the anaerobic secretome bioreactor environment.

19. A method for biogas production in a system comprising an anaerobic secretome bioreactor environment coupled to an anaerobic digestion reactor environment, the method comprising:
pretreating, in the anaerobic secretome bioreactor environment, biomass comprising lignocellulose, the pretreating performed using at least one type of microorganism selected from extremophile thermophilic anaerobic microorganisms that are essentially acidogens and acetogens that produce a secretome of exozymes that solubilize and metabolize a substantial portion of the lignocellulose through hydrolysis, acidoqenesis, and acetoqenesis; and
treating, in the anaerobic digestion reactor environment, the pretreated biomass, the treating performed using non-thermophilic anaerobic microorganisms so as to produce methane through methanogenesis of the pretreated biomass; and
recycling contents or heat between the anaerobic secretome bioreactor environment and the anaerobic digestion reactor environment.

20. The method of claim 19 further comprising pasteurizing the pretreated biomass prior to the treating, the pasteurizing performed at a thermophilic temperature between 70 to 85 degrees Celsius and under essentially acidogenic, acetogenic, and non-methanogenic conditions, such that the pasteurized pretreated biomass is substantially free of non-thermophilic microorganisms.

\* \* \* \* \*